United States Patent
Dasi et al.

(10) Patent No.: US 12,268,596 B2
(45) Date of Patent: Apr. 8, 2025

(54) TRI-LEAFLET PROSTHETIC HEART VALVE

(71) Applicant: Ohio State Innovation Foundation, Columbus, OH (US)

(72) Inventors: Lakshmi Prasad Dasi, Dublin, OH (US); Atieh Yousefi Koupaei, Columbus, OH (US); Megan Kristine Heitkemper, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 38 days.

(21) Appl. No.: 18/060,199

(22) Filed: Nov. 30, 2022

(65) Prior Publication Data

US 2023/0146082 A1    May 11, 2023

Related U.S. Application Data

(62) Division of application No. 16/625,442, filed as application No. PCT/US2018/040415 on Jun. 29, 2018, now abandoned.

(60) Provisional application No. 62/527,632, filed on Jun. 30, 2017.

(51) Int. Cl.
*A61F 2/24*        (2006.01)

(52) U.S. Cl.
CPC ...... *A61F 2/2418* (2013.01); *A61F 2240/001* (2013.01); *A61F 2250/0037* (2013.01)

(58) Field of Classification Search
None
See application file for complete search history.

(56) References Cited

U.S. PATENT DOCUMENTS

| | | | |
|---|---|---|---|
| 5,469,868 A | 11/1995 | Reger | |
| 5,928,281 A * | 7/1999 | Huynh | A61F 2/2412 623/2.14 |
| 6,936,067 B2 * | 8/2005 | Buchanan | A61F 2/2409 623/2.14 |

(Continued)

FOREIGN PATENT DOCUMENTS

| | | |
|---|---|---|
| DE | 1939121 A1 | 3/1970 |
| WO | 2009108615 A1 | 9/2009 |

(Continued)

OTHER PUBLICATIONS

International Search Report and Written Opinion issued in PCT application No. PCT/US2018/040415 mailing date Jan. 17, 2019.

(Continued)

*Primary Examiner* — Jacqueline Woznicki
(74) *Attorney, Agent, or Firm* — Benesch Friedlander Coplan & Aronoff LLP

(57) ABSTRACT

A prosthetic heart valve includes a first upper frame portion and a stent frame connected to the first upper frame portion via at least two stent frame extensions. The stent frame includes a base and at least two stent posts extending upwardly from the base towards the first upper frame portion. The first upper frame portion, the base, and the at least two stent posts each has an inner surface and an outer surface. The prosthetic heart valve also includes at least one sheet of leaflet material configured to encircle the stent frame and weave through the stent frame between the first upper frame portion and the base.

16 Claims, 26 Drawing Sheets

(56) References Cited

U.S. PATENT DOCUMENTS

| | | | |
|---|---|---|---|
| 10,441,415 B2* | 10/2019 | Johnson | A61F 2/2418 |
| 2002/0052651 A1* | 5/2002 | Myers | A61F 2/2415 |
| | | | 623/2.15 |
| 2002/0173842 A1 | 11/2002 | Buchanan | |
| 2005/0137681 A1* | 6/2005 | Shoemaker | A61F 2/06 |
| | | | 623/1.23 |
| 2006/0047338 A1 | 3/2006 | Jenson | |
| 2007/0050021 A1* | 3/2007 | Johnson | A61F 2/2418 |
| | | | 623/2.14 |
| 2008/0294248 A1* | 11/2008 | Yang | A61F 2/2418 |
| | | | 623/2.17 |
| 2009/0054973 A1* | 2/2009 | Johnson | A61F 2/2412 |
| | | | 623/2.38 |
| 2009/0157175 A1* | 6/2009 | Benichou | A61F 2/2415 |
| | | | 623/2.18 |
| 2010/0036484 A1 | 2/2010 | Hariton et al. | |
| 2010/0168839 A1 | 7/2010 | Braido et al. | |
| 2010/0185277 A1 | 7/2010 | Braido et al. | |
| 2010/0249915 A1 | 9/2010 | Zhang | |
| 2011/0238168 A1 | 9/2011 | Pellegrini et al. | |
| 2011/0282440 A1* | 11/2011 | Cao | A61F 2/2418 |
| | | | 623/2.18 |
| 2011/0295363 A1* | 12/2011 | Girard | A61F 2/2412 |
| | | | 623/1.26 |
| 2012/0078357 A1 | 3/2012 | Conklin | |
| 2012/0101567 A1* | 4/2012 | Jansen | A61F 2/2412 |
| | | | 623/1.36 |
| 2013/0131793 A1 | 5/2013 | Quadri et al. | |
| 2013/0197631 A1 | 9/2013 | Bruchman | |
| 2014/0277411 A1 | 9/2014 | Börtlein et al. | |
| 2015/0088250 A1* | 3/2015 | Zeng | A61F 2/2418 |
| | | | 623/2.12 |
| 2015/0196688 A1 | 7/2015 | James et al. | |
| 2016/0067038 A1 | 3/2016 | Park et al. | |
| 2016/0074161 A1 | 3/2016 | Bennett | |
| 2016/0143730 A1 | 5/2016 | Kheradvar | |
| 2016/0235561 A1 | 8/2016 | Wrobel et al. | |
| 2017/0065408 A1* | 3/2017 | Grundeman | A61F 2/2412 |
| 2017/0252163 A1 | 9/2017 | Kheradvar | |
| 2018/0021129 A1 | 1/2018 | Peterson et al. | |
| 2020/0121456 A1* | 4/2020 | Johnson | A61F 2/2418 |
| 2021/0145572 A1 | 5/2021 | Dasi et al. | |
| 2021/0145573 A1 | 5/2021 | Dasi et al. | |

FOREIGN PATENT DOCUMENTS

| | | |
|---|---|---|
| WO | 2014008207 A1 | 1/2014 |
| WO | 2014170870 A2 | 10/2014 |

OTHER PUBLICATIONS

International Preliminary Report on Patentability issued in PCT application No. PCT/US2018/040415 completed Jan. 16, 2019.

Extended European Search Report Issued in European application No. 18825037.7, dated Feb. 18, 2021.

First Examination Report issued in Indian patent application No. 202047003605, dated Feb. 25, 2022.

Non-Final Office Action issued in U.S. Appl. No. 16/625,442, dated Sep. 2, 2022.

Non-Final Office Action issued in U.S. Appl. No. 16/625,442, dated Nov. 5, 2021.

Examination Report issued in AU patent application No. 2018294420, dated May 1, 2023.

* cited by examiner

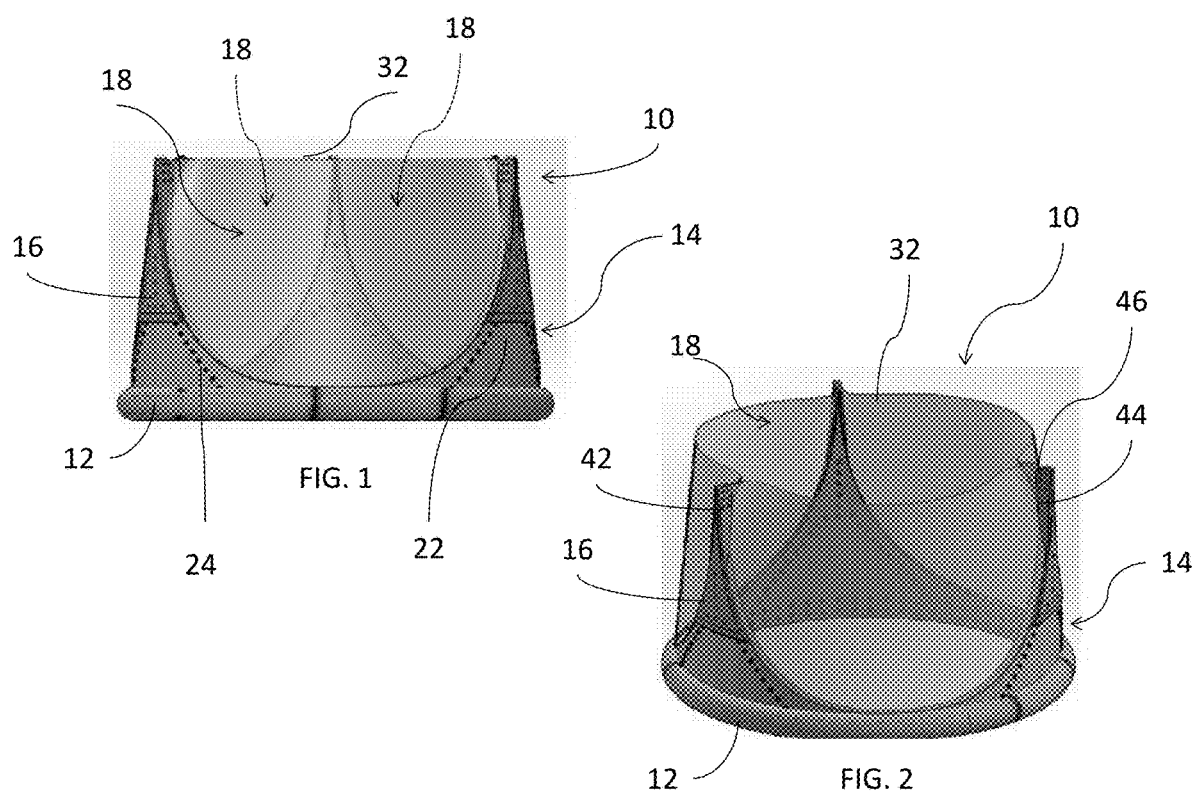

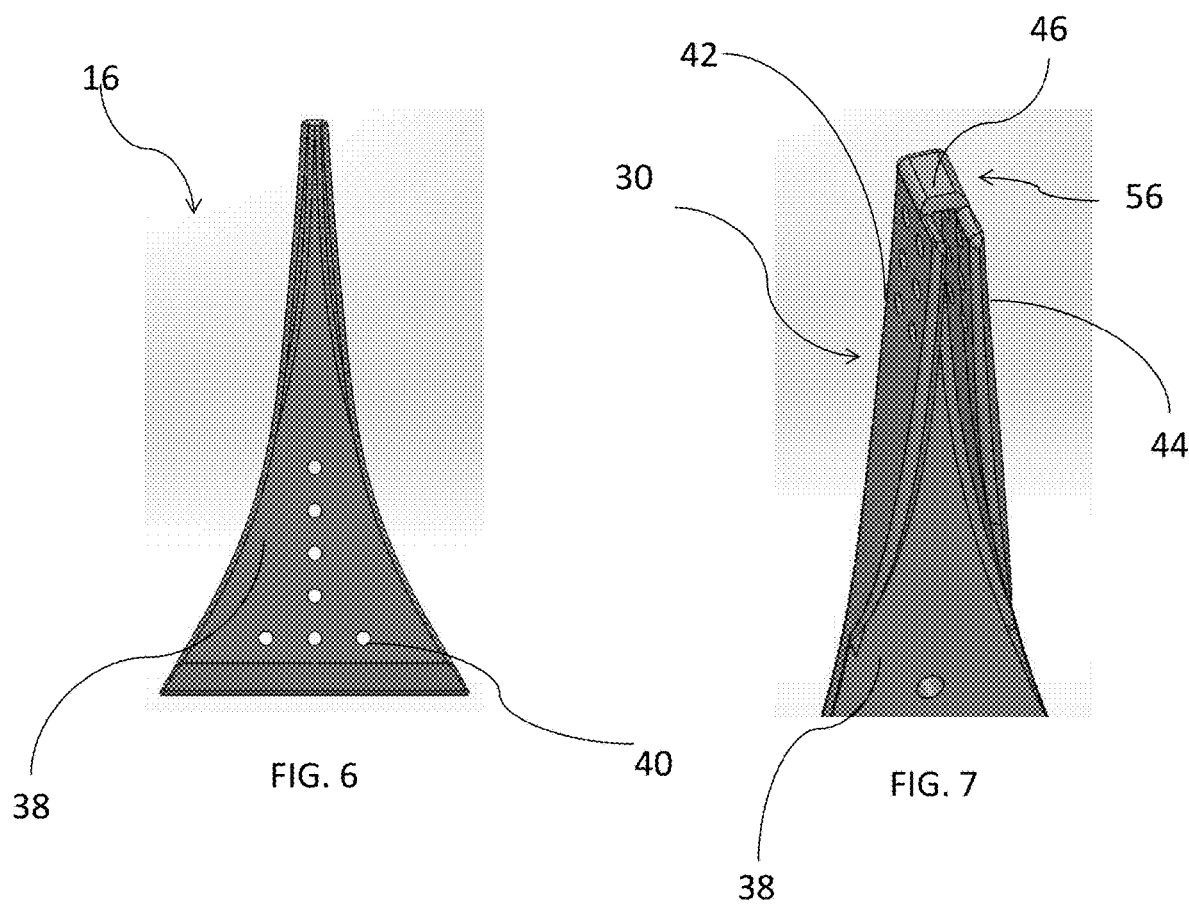

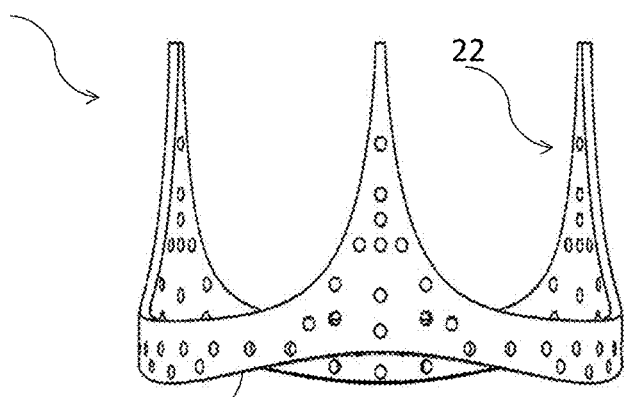
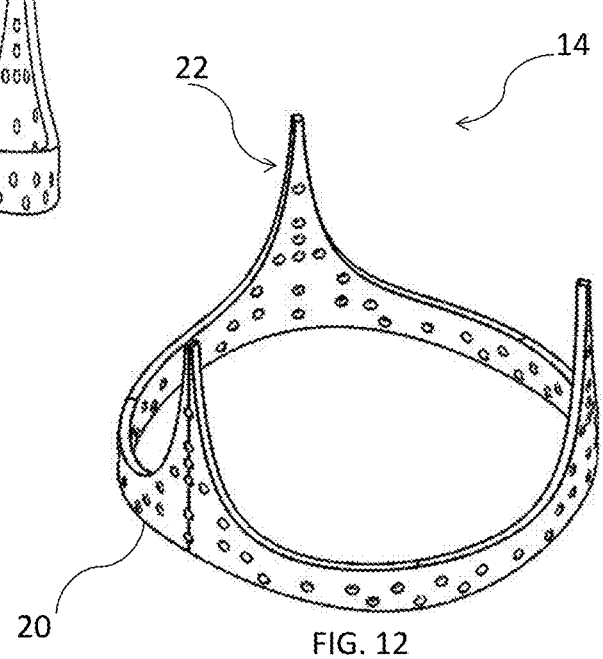
FIG. 11
FIG. 12

TRI-LEAFLET PROSTHETIC HEART VALVE

CROSS REFERENCE OF RELATED APPLICATION

This application is a divisional application and claims the benefit of U.S. application Ser. No. 16/625,442 filed Dec. 20, 2019, which is a national stage application of PCT/US2018/040415 filed Jun. 29, 2018, which claims the benefit of the U.S. Provisional Patent Application No. 62/527,632 filed Jun. 30, 2017, which are each incorporated herein by reference in [its] their entirety.

GOVERNMENT SPONSORSHIP

This invention was made with government support under grant/contract numbers EB014255 and HL 119824 awarded by the National Institutes of Health. The government has certain rights in the invention.

FIELD OF THE INVENTION

The present invention relates to the manufacture and use of a prosthetic valve for use in the human heart. More specifically, the invention relates to the manufacture and use of a valve that may be surgically implanted into the heart of a patient in order to replace a native tri-leaflet heart valve.

BACKGROUND

Heart valve replacement is the second most common cardiac operation performed in the United States. Currently, over four million people are diagnosed with heart valve disorder across the world, each year. Moreover, heart disease is prevalent in about 2.5% of the overall United States population, and 10.4% of its elderly population.

Typically, prosthetic heart valves used in aortic and mitral heart valve replacement procedures are either mechanical or bioprosthetic. However, these valves introduce significant risk of thromboembolism, requiring the patient to undergo lifelong anticoagulation therapy, or the patient become more prone to valve degeneration and tissue failure, requiring reoperation. It would be useful to produce a prosthetic heart valve that would be durable, while not necessitating anticoagulation therapy.

SUMMARY

A prosthetic heart valve includes a first upper frame portion and a stent frame connected to the first upper frame portion via at least two stent frame extensions. The stent frame includes a base and at least two stent posts extending upwardly from the base towards the first upper frame portion. The first upper frame portion, the base, and the at least two stent posts each has an inner surface and an outer surface. The prosthetic heart valve also includes at least one sheet of leaflet material configured to weave through the stent frame between the first upper frame portion and the base.

A prosthetic heart valve includes a stent frame with a first upper frame portion, a base, and at least two stent posts extending upwardly from the base; wherein the base is connected to the first upper frame portion by the at least two stent posts, and wherein the first upper frame portion, the base, and the at least two stent posts each has an inner surface and an outer surface; and at least one sheet of leaflet material configured to weave through the stent frame from the outer surface to the inner surface between the first upper frame portion and the base of the stent frame.

In another embodiment, the at least one sheet of leaflet material is disposed on the outer surface of the base and of the at least two stent posts, and at least a portion of the at least one sheet of leaflet material is tucked under the first upper frame portion between the first upper frame portion and the base and is disposed on the inner surface of the upper frame portion.

In another embodiment, the at least one sheet of leaflet material is disposed on the inner surface of the base and of the at least two stent posts, and at least a portion of the at least one sheet of leaflet material is tucked in under the first upper frame portion between the first upper frame portion and the base.

In another embodiment, the first upper frame portion has a shape that is substantially similar to an upper edge of the base.

In another embodiment, the stent frame further comprises a second upper frame portion connected to the first upper frame portion, and wherein the second upper frame portion has a shape that is substantially similar to an upper edge of the first upper frame portion. The stent frame may also include a third upper frame portion connected to the second upper frame portion, wherein the third upper frame portion has a shape that is substantially similar to an upper edge of the second upper frame portion. Moreover, the at least one sheet of leaflet material weaves through the stent frame between the first upper frame portion and the second upper frame portion and/or between the second upper frame portion and the third upper frame portion.

The base may further have a lower edge that is substantially similar to a lower edge of the first upper frame portion. And, the at least two stent posts have at least two heights different from one another.

In one embodiment, the at least one sheet of leaflet material is a continuous sheet of leaflet material. In another embodiment, the continuous sheet of leaflet material comprises an upper portion having at least two arches extending upwardly therefrom. In another embodiment, the continuous sheet of leaflet material comprises one or more spacings in the upper portion, wherein each of the one or more spacings is disposed between two of the at least two arches. Moreover, the at least one sheet of leaflet material comprises a polymer material that may be linear low density polyethylene, polytetrafluoroethylene, low-density polyethylene, polyethylene terephthalate, polypropylene, polyurethane, polycaprolactone, polydimethylsiloxane, polymethylmethacrylate, polyoxymethylene, thermoplastic polyurethane, and combinations thereof. The leaflet material may also include hyaluronic acid. And, the at least one sheet of leaflet material may include a bioprosthetic material In one embodiment, the stent frame has a height and an inner diameter, and wherein the ratio of height to diameter is from about 0.5 to about 0.9. The at least two arches may have a height, and wherein the ratio of the height of the at least two arches to the inner diameter of the stent frame is from about 0.05 to about 0.12.

Finally, the at least one sheet of leaflet material has a three dimensional curvature and wherein the leaflet material is two dimensional when heated to form a rounded leaflet.

DESCRIPTION OF THE DRAWINGS

FIG. 1 is a front view of one embodiment of a prosthetic heart valve in an open position;

FIG. 2 is a perspective view of the prosthetic heart valve of FIG. 1;

FIG. 6 is a front view of one embodiment of a clip for use in a prosthetic heart valve;

FIG. 7 is an enlarged rear perspective view of one embodiment of the top portion of a clip for use in a prosthetic heart valve;

FIG. 11 is a front view of another embodiment of a stent frame for use in a prosthetic heart valve;

FIG. 12 is a perspective view of the stent frame of FIG. 11;

DETAILED DESCRIPTION

Figure 3:
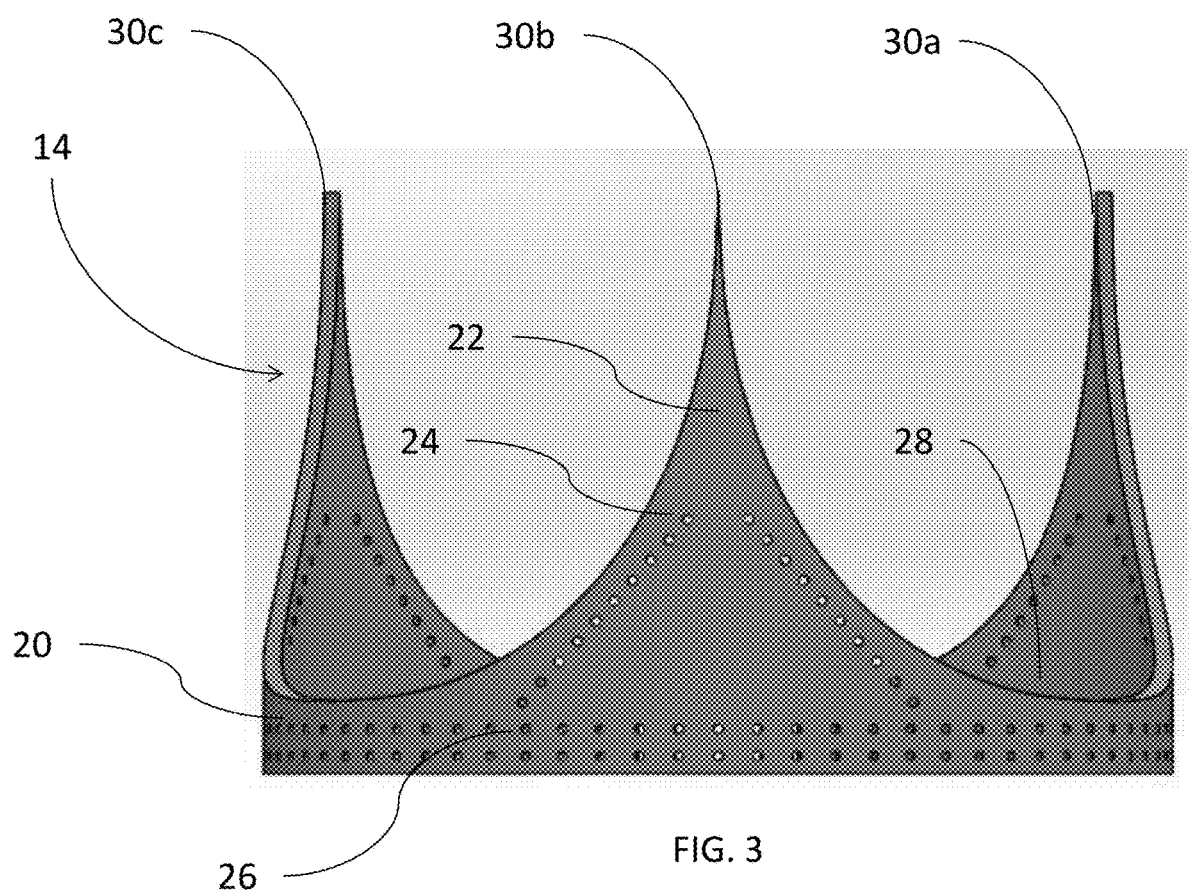
FIG. 3 is a front view of one embodiment of a stent frame for use in a prosthetic heart valve.

A prosthetic heart valve (PHV), including a stent frame and leaflet material, having a tri-leaflet design for use to replace either a failing or damaged native aortic or mitral heart valve in a patient is provided. Although we will refer to a tri-leaflet design, it should be apparent to one of skill in the art that any number of leaflets may be created using the PHV described herein. In one embodiment, the PHV will provide a prosthetic valve with a higher effective orifice compared to other prosthetic valves that are commercially available. The PHV will also provide improved flow characteristics through the geometric design of both the stent frame and the leaflet.

In one embodiment, the design of the stent frame in combination with the design of the leaflets enable improved performance over other commercially available prosthetic valves. For example, the design of the leaflet and/or the manner in which the leaflet is disposed on the stent frame may improve durability of the PHV, reduce the number of sutures required to assemble the PHV, and/or improve leaflet coaptation.

FIGS. 1 and 2 show illustrate a first embodiment of the PHV 10. In the embodiment, the PHV 10 includes a suture ring 12, a stent frame 14, a plurality of stent clips 16, and a sheet of leaflet material 32 which may be disposed between the stent frame 14 and the stent clips 16 in order to form at least two leaflets 18.

In one embodiment the stent frame 14 may be formed of a single piece of material, however it should be recognized that multiple pieces of stent material may be used to create a single stent frame 14. Referring now to FIG. 3, the stent frame 14 may be laser cut from a cylindrical tube or pipe. Alternatively, the stent frame 14 may be laser cut from a flat piece of material, rolled into the desired shape, and affixed to hold the shape at either of the free ends (not shown). In another embodiment, the stent frame may be "printed" or molded using additive manufacturing techniques known to those of skill in the art.

Generally, the stent frame 14 includes a generally circular base 20 defining the valve orifice of the PHV 10 and at least two, and in one embodiment three, stent posts 22 extending upwardly from the base 20. The stent frame 14 may also include a plurality of suture openings 24 in order to facilitate attachment of the stent frame 14 to the leaflet material 32 (as shown in FIG. 1).

The stent frame 14 may be made of stainless steel, nitinol, cobalt chromium or other suitable material. It should be understood that the base 20 of the frame 14 may be generally circular in nature or it may be elliptical, oval, or other shape suitable to the curvature of the patient's valve annulus. As shown in FIGS. 11 and 12, the base 20 may alternatively have an undulating, rather than straight, shape to better fit the anatomical curvature of a patient's vessel. It should also be understood that the stent posts 22 that extend from the base 20 of the stent frame 14 may be placed equidistant around the circumference of the stent frame 14 or they may be placed at irregular intervals in order to more closely mimic the natural shape of the patient's native valve. The stent frame 14 maybe be produced in varying sizes, depending on the size of the patient's heart. For example, the base 20 of the stent frame 14 may have a diameter of 17, 19, 21, 23, 25, 27, 29, or 31 millimeters (mm). The base of the stent frame 14 may also include an additional plurality of suture openings 26 intended to facilitate attachment of the frame 14 to the suture ring 12 (as shown in FIGS. 1 and 2).

The stent posts 22 generally extend upwards from the stent base 20. In one embodiment, the stent posts 22 have a curved triangular shape, creating scalloped edges 28, extending between top point 30(a) and top point 30(b), top point 30(b) and top point 30(c), and top point 30(c) and top point 30(a). The stent posts 22, when wrapped with the leaflet material 32, define the leaflets 18 (or cusps) of the PHV 10, as shown in FIG. 1.

Figure 4:
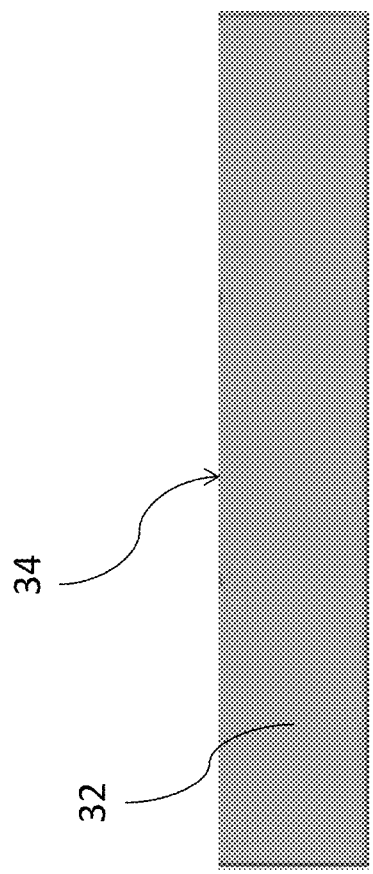
FIG. 4 is a plan view of a rectangular pieces of leaflet material before it is attached to the stent frame.
Figure 5:
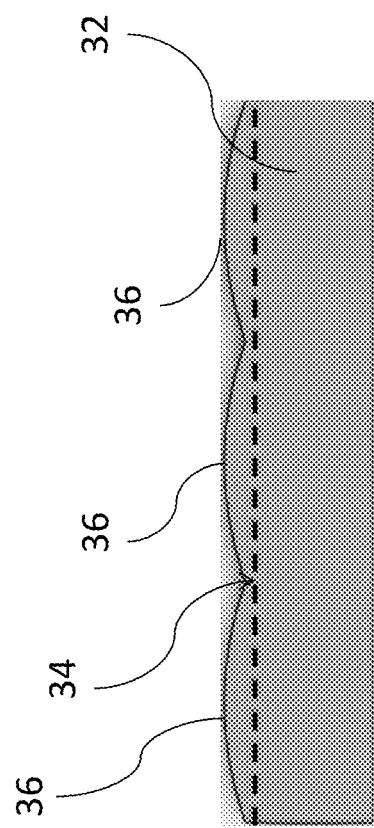
FIG. 5 is a plan view of a piece of leaflet material including an arched upper edge.

Referring now to FIGS. 1, 4, and 5, the leaflets 18 of the PHV 10 may be created using a single piece of polymeric or bioprosthetic (such as porcine or bovine pericardium) material 32. It will also be understood that the leaflets 18 may also be created using separate pieces of leaflet material affixed between each set of stent posts 22.

As shown in FIG. 4, in one embodiment, a continuous sheet of leaflet material 32 may include an upper edge portion 34 and be generally rectangular in shape, or as shown in FIG. 5, may include an upper edge portion 34 having at least one arch 36 extending upwardly therefrom.

The leaflet material 32 may be made of a polymeric material, such as linear low density polyethylene (LLDPE), polytetrafluoroethylene (PTFE), low-density polyethylene (LDPE), polyethylene terephthalate (PET), polypropylene (PP), polyurethane, polycaprolactone (PCL), polydimethylsiloxane (PDMS), polymethylmethacrylate (PMMA), polyoxymethylene (POM), thermoplastic polyurethane (TPU), and combinations thereof.

In one embodiment, the leaflet material 32 may be made of a polymeric material, such as LLDPE, that includes hyaluronic acid to prevent blood clot and thrombosis formation. An example of this material is disclosed in U.S. application Ser. No. 14/381,332, entitled Glycosaminoglycan and Synthetic Polymer Material for Blood-Contacting Applications, which is incorporated herein by reference in its entirety.

As shown in FIG. 1, the leaflet material 32 may be wrapped about and sutured to the outer circumference of the stent frame 14 through the plurality of suture openings 24 in the stent posts 22, forming three leaflets 18 resembling the tri-leaflet aortic heart valve in the normally open position. It should be understood that a PHV may also be made having two leaflets to mimic the bi-leaflet mitral heart valve.

By using a single continuous piece of leaflet material mounted around the stent frame 14, the number of sutures required to assemble the leaflets 18 is reduced. However, it should be appreciated that multiple pieces of leaflet material 32 may be mounted about the outer circumference of the stent frame 14.

In one embodiment, the suture ring 12 may be covered in a suitable material, such as Dacron®, disposed atop the leaflet material 32, and affixed to the stent frame 14 with sutures or other means, such as the use of a suitable adhesive. By covering only the suture ring 12 with Dacron® the outer and inner diameter of the PHV are reduced, allowing for a larger valve area and, consequently, a higher effective orifice area.

Referring again to FIG. 1, once the leaflet material 32 is affixed to the stent frame 14, stent clips 16 are affixed to each of the stent posts 22 through the suture openings or with adhesive, such that the leaflet material 32 is disposed there between. The stent clips 16 may be formed of stainless steel, nitinol, or other suitable material.

Referring specifically to FIGS. 6 and 7, in one embodiment, the stent clips 16 have a facial surface 38 and suture openings 40 that may be laser cut to mimic the shape of the outer surface of stent posts 22. Referring to FIG. 7, the stent clips 16 may also include a top point portion 56 that includes a left flange 42, right flange 44, and top flange 46 that extend from the facial surface 38 of the stent clips 16 toward the inner surface (not shown) of the stent frame 14.

In another embodiment, the outer surface of the stent clips 16 may be covered with Dacron® or other suitable material (not shown) in order to provide smooth contact between the stent posts 22 and the vessel wall.

Figure 8:
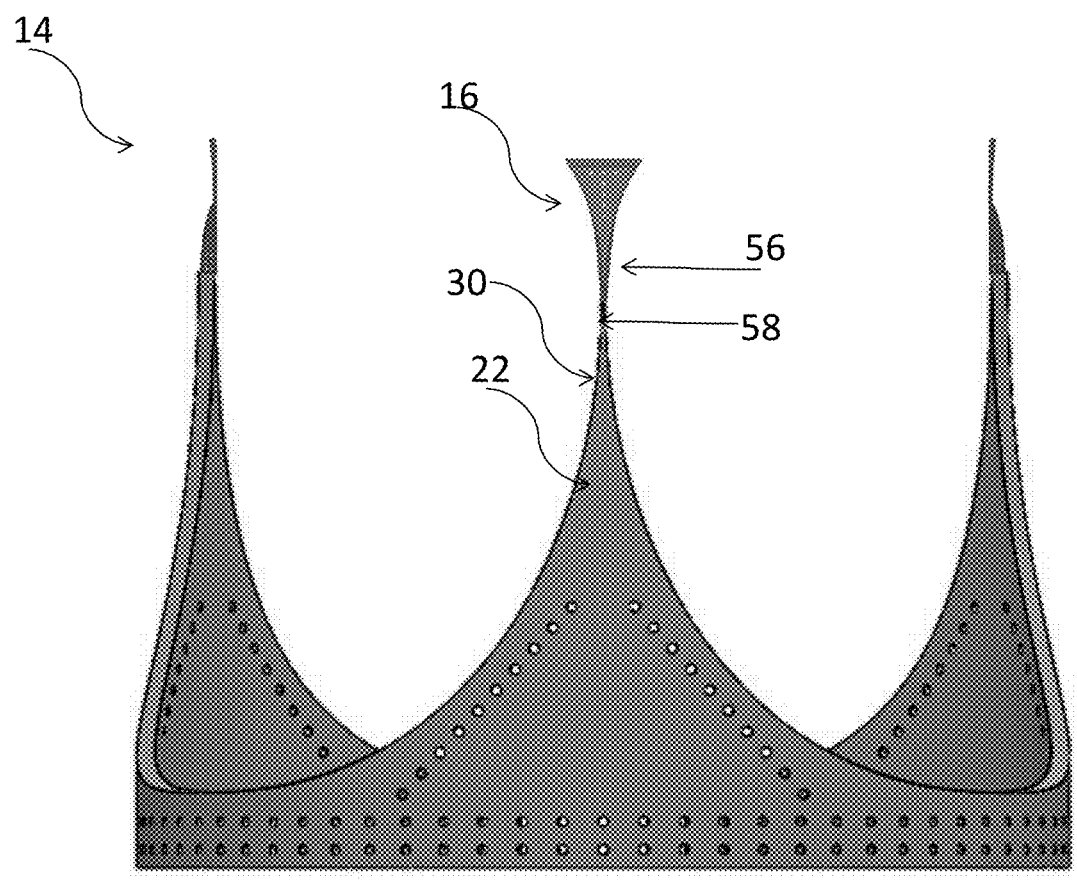
FIG. 8 is a front view of another embodiment of a stent clip and stent frame for use in a prosthetic heart valve.

As shown in FIGS. 6 and 7, in one embodiment, the stent clips 16 may be distinct pieces, formed separately from the stent frame 14. In another embodiment, as shown in FIG. 8, the stent clips 16 may be integrally formed with the stent frame 14. In this embodiment, the top point portion 56 of each stent clip 16 may be connected to the top point portion 30 of the respective stent post 22. In this embodiment, the stent clips 16 can be folded at the connection point 58, with the facial surface 38 of the stent clip 16 facing the outer surface of the stent post 22. The stent clip 16 is then affixed to the stent posts 22 through the respective suture openings or with adhesive, sandwiching the leaflet material 32 there between, as described above.

As shown in FIG. 2, the stent clip flanges (42, 44, 46) are designed to gather the leaflet material 32 at the stent post 22, enabling the leaflets 18 to mimic the function of a native aortic heart valve cusp, opening and closing with the flow of blood through the PHV 10. Specifically, the stent clips 16 provide improved commissure coaptation adjacent to the sent posts and enhance closing dynamics of the leaflets.

Figure 9:
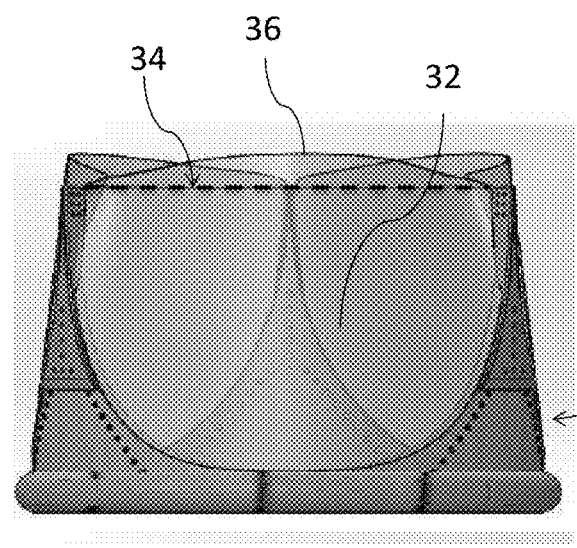
FIG. 9 is a front view of another embodiment of a prosthetic heart valve.
Figure 10:
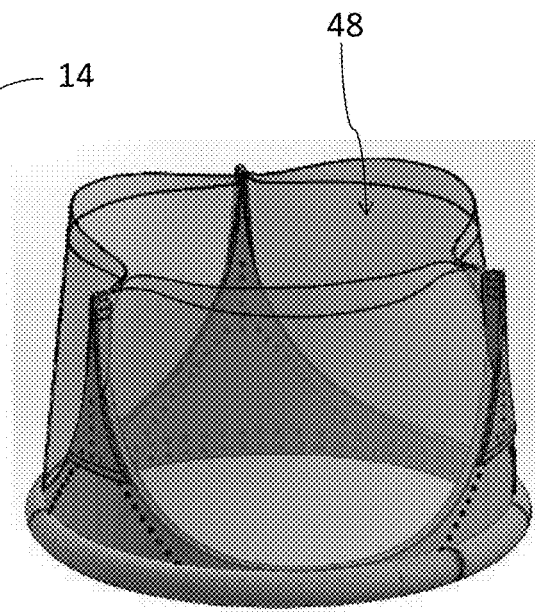
FIG. 10 is a perspective valve of the prosthetic heart valve of FIG. 8.

Referring to FIGS. 5, 9, and 10, in another embodiment, the leaflet material 32 may include an upper edge portion 34 with a plurality of arches 36. It should be understood that the arches 36 may be formed integrally with the single sheet of leaflet material 32 or may be attached to the upper edge portion 34 after the material is formed. The arches 36 on the upper edge portion 34 provide arched leaflets 48 (as shown in FIG. 9), when wrapped around the stent frame 14. Through the use of arched leaflets 48, it was discovered that flow reattachment is facilitated and recirculation regions that are directly related to thrombus formation are decreased. In addition, the use of arched leaflets 48 provide an improved leaflet coaptation.

In another embodiment, once the sheet of leaflet material 32 is installed onto the stent frame 14, the leaflets 18 may be further formed by applying a combination of heat and pressure to the once the planar leaflets 18. This treatment can be used to further change the shape of the leaflets 18 into a three dimensional configuration (as is the case for native valve leaflets). In one embodiment, vacuum pressure is applied to the formed PHV 10 on the upstream side of the PHV to force the leaflets 18 to close and then heat is applied from the downstream side in order to make the polymer (which is a thermoplastic) relax and stretch under the forces exerted by the vacuum. The resulting shape of the leaflets 18 may more closely resemble the patent's native leaflet shape.

In other set of embodiments, the stent frame 14 may have various other designs, while the leaflet material 32 may be secured to the stent frame 14 in generally the same or similar manner as set forth above. In one embodiment, as shown in FIGS. 11 and 12, the base 20 of the stent frame 14 may have an undulating, rather than straight, shape to better fit the anatomical curvature of a patient's vessel.

Figure 17:
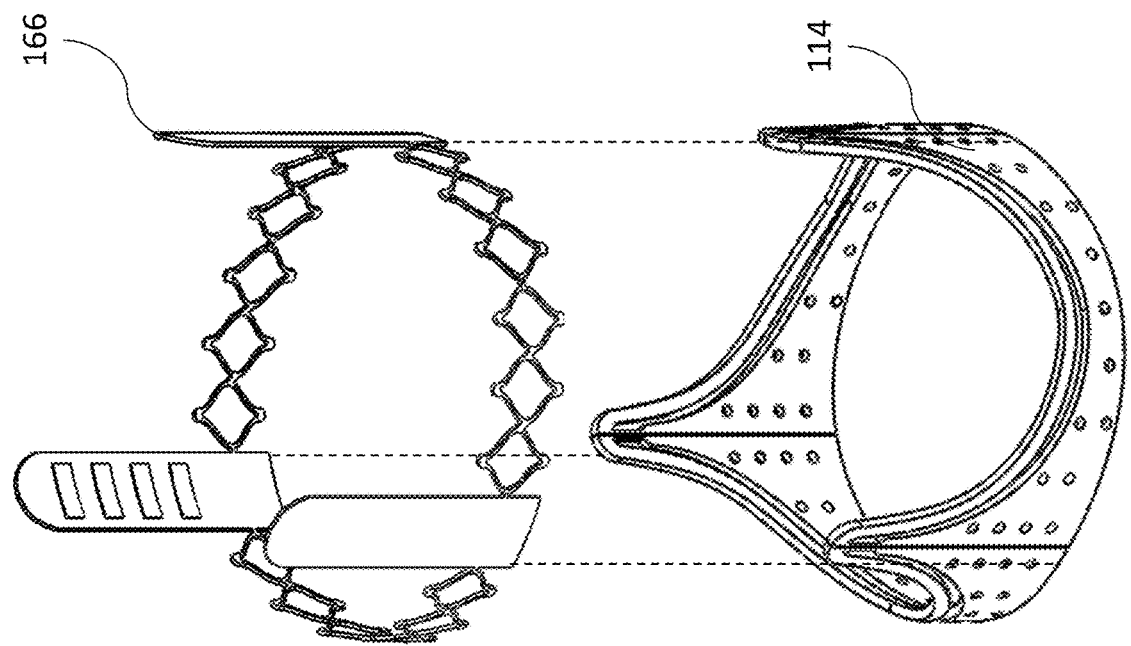
FIG. 17 is an exploded view of an alternative embodiment of a stent frame and an outer cover.

In another embodiment, as shown in FIG. 17, an outer cap 166 may be used to secure the leaflet material to the stent frame 114. In this embodiment, the outer cap 166 may be disposed to fit over the outer surface of the stent frame 114, sandwiching the leaflet material between the frame 114 and the cap 166.

Figure 13:
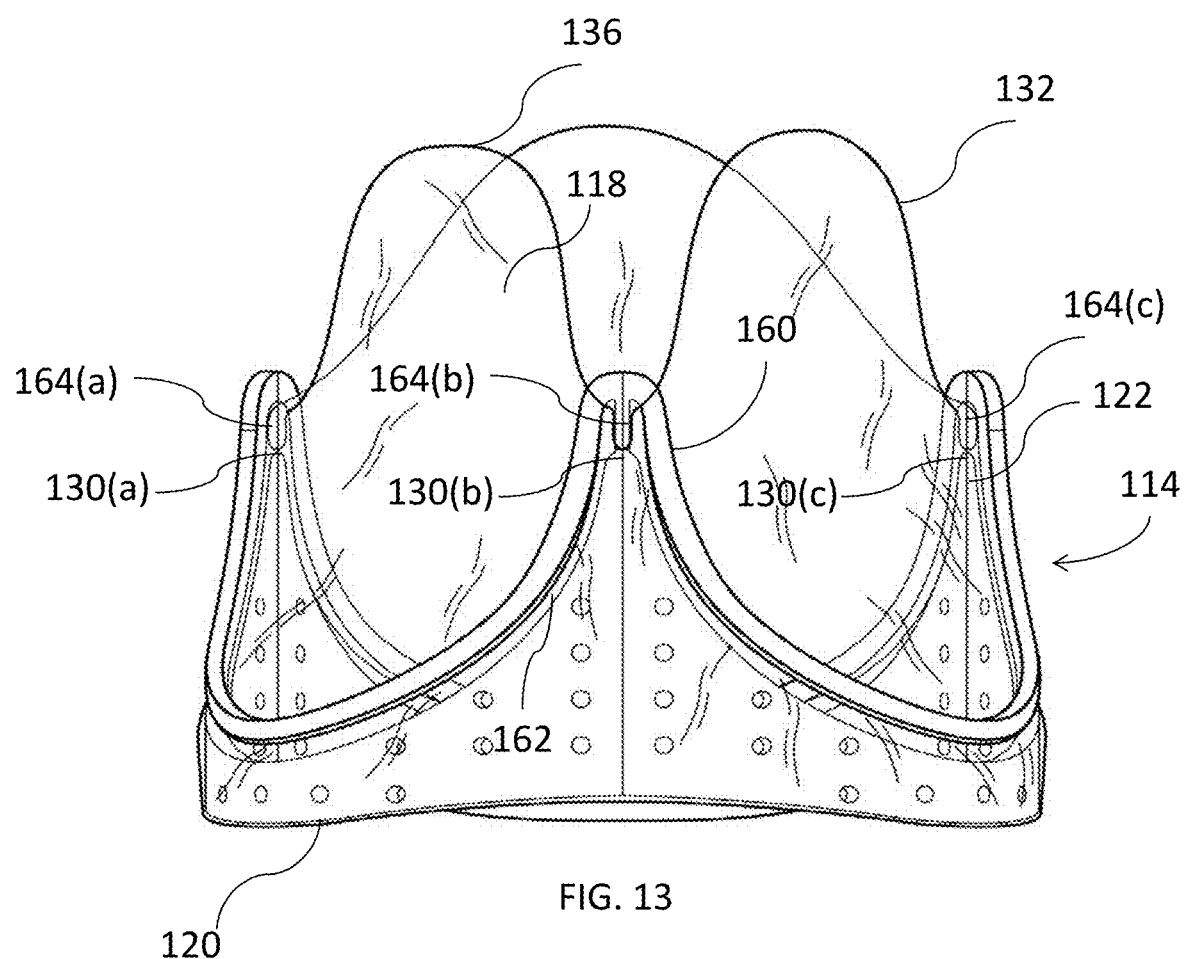
FIG. 13 is a front view of an alternative embodiment of a stent frame for use in a prosthetic heart valve.

In another set of embodiments, as shown in FIGS. 13-16, and 18-24, the PHV 10 may have a stent frame that includes an upper frame portion, a base, and at least two stent posts (e.g., two stent posts, three stent posts, etc.). Referring to FIG. 13 for example, the stent frame 114 includes an upper frame portion or a first upper frame portion 160, a base 120, and stent posts 122 (e.g., at least two stent posts 122). Generally, the upper frame portion 160 has a shape that mimics that of the upper edge 162 of and between the stent posts 122. The upper frame portion 160 connects to the stent posts 122 only at each of the top points 130(a)-(c) by stent frame extensions 164(a)-(c), respectively.

Figure 14:
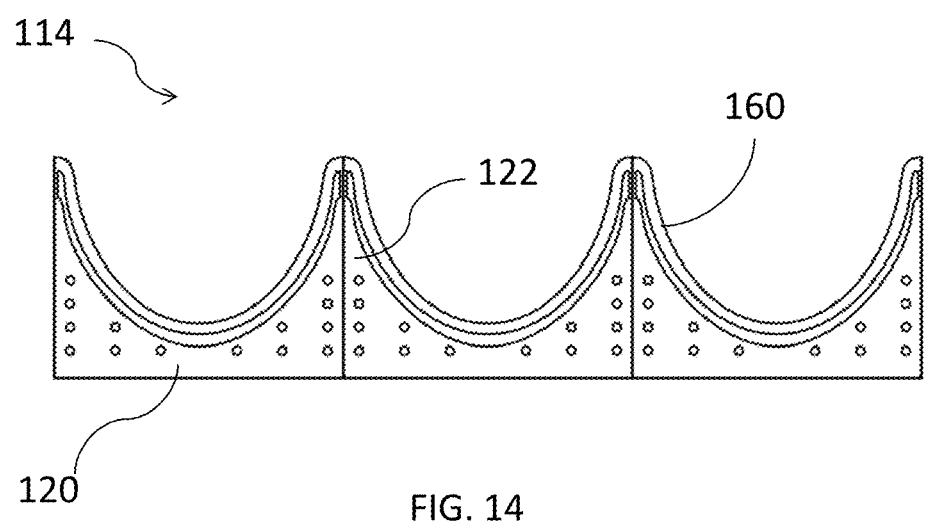
FIG. 14 is a plan view of the stent frame of FIG. 13.
Figure 15:
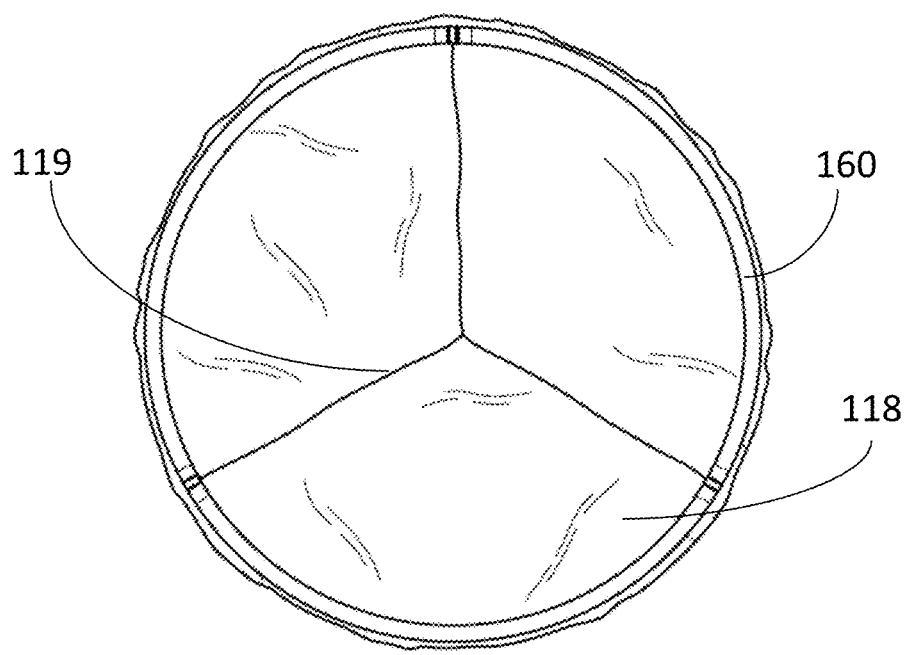
FIG. 15 is top view of the prosthetic heart valve of FIG. 13 with the leaflets in a closed position.

In this embodiment, the leaflet material may be attached to the stent frame 114 as described above with the use of stent clips. However, in an alternative embodiment, as shown in FIGS. 13, 14 and 15 the leaflet material may be attached to the stent frame 114 by weaving the single piece of leaflet material 132 between the stent frame 114 and the upper frame portion 160 such that either the bottom portion of the leaflet material (as shown in FIGS. 4 and 5) is disposed against the inner surface of the stent frame 114 and the upper portion of the leaflet material is disposed against the outside surface of the upper frame portion 160 or the bottom portion of the leaflet material is disposed against the outer surface of the stent frame 114 and the upper portion is disposed against the inner surface of the upper frame portion 160. The leaflet material may then be further secured to the stent frame 114 using sutures or adhesives, as described above.

While reducing the number of sutures needed to secure the leaflet material to the frame 114, this embodiment also protects the formed leaflets (not shown) from possible tearing as they expand and contract over the top of the upper frame portion 160. Moreover, in embodiments that the leaflet material 132 is woven through the stent frame 114 as shown in FIGS. 13 and 15, the upper frame portion 160 gathers the leaflet material 132 and enables the leaflets 118 to mimic the function of a native aortic heart valve cusp, opening and closing with the flow of blood through the PHV 10. As such, the stent clip may be eliminated. The leaflet material 132 may be further adhered to the outside of the stent frame 114 by using a minimal amount of sutures.

Figure 16:
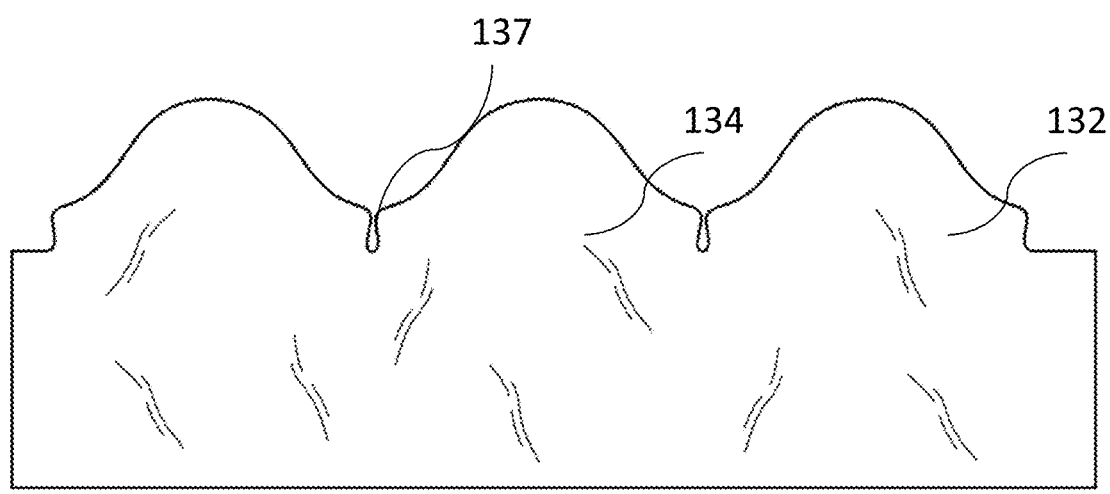
FIG. 16 is a plan view of a piece of leaflet material before it is attached to the stent frame of FIG. 13.

In another embodiment of the leaflet material, as shown in FIG. 16, the continuous sheet of leaflet material 132 may include one or more spacings or notches 137 in the upper edge portion 134. This embodiment of leaflet material is particularly useful with the stent frames shown and described in FIGS. 13-15. For example, each of the one or more spacing or notches 137 is between every two directly adjacent arches 136. The one or more spacings 137 may improve coaptation of the leaflets 118 when wrapped around stent frame extensions 164. For example, the one or more spacing 137 may help accommodating the opening and closing motions of the leaflets 118, such that the commissures 119 meet with better conformity to achieve better coaptation and ensure minimal reverse flow of the blood when the leaflets 118 are closed, as shown in FIG. 15.

Figure 18:
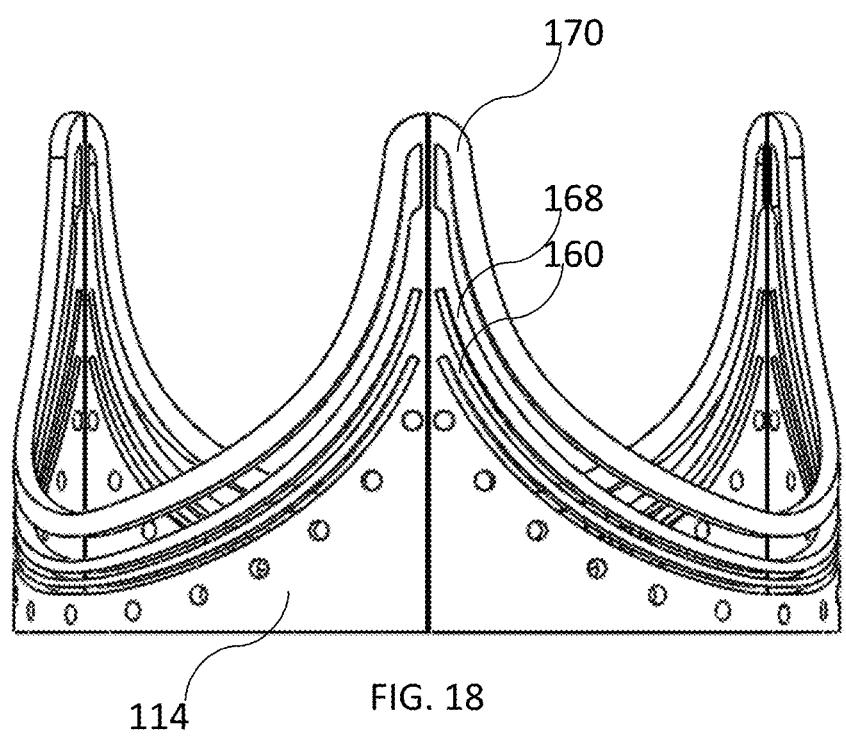
FIG. 18 is a front view of an alternative embodiment of a stent frame.
Figure 19:
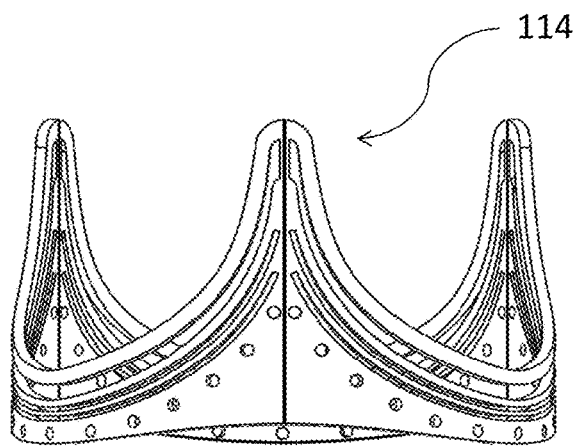
FIG. 19 is a front view of an alternative embodiment of a stent frame.
Figure 20:
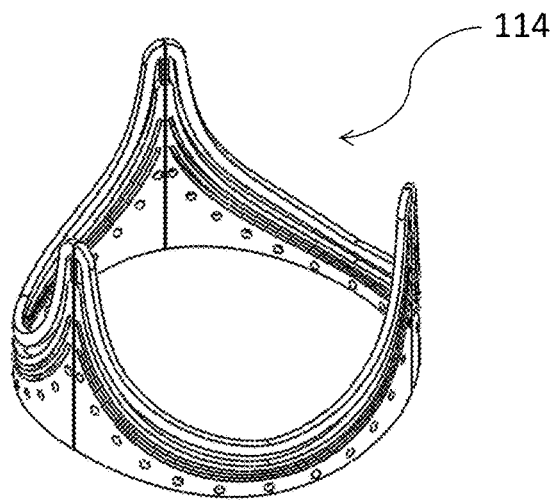
FIG. 20 is a perspective view of the stent frame of FIG. 19.
Figures 21, 22:
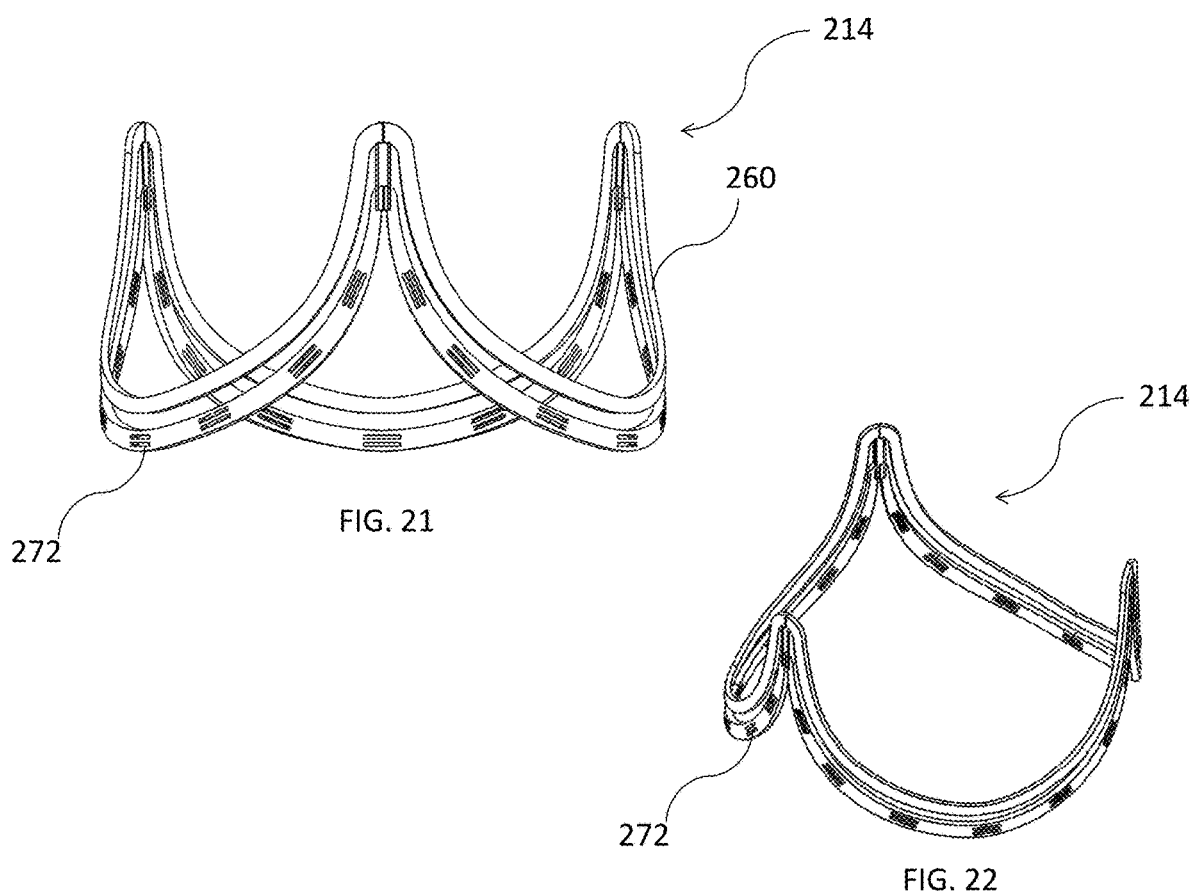
FIG. 21 is a front view of an alternative embodiment of a stent frame.
FIG. 22 is a perspective view of the stent frame valve of FIG. 21.
Figure 23:
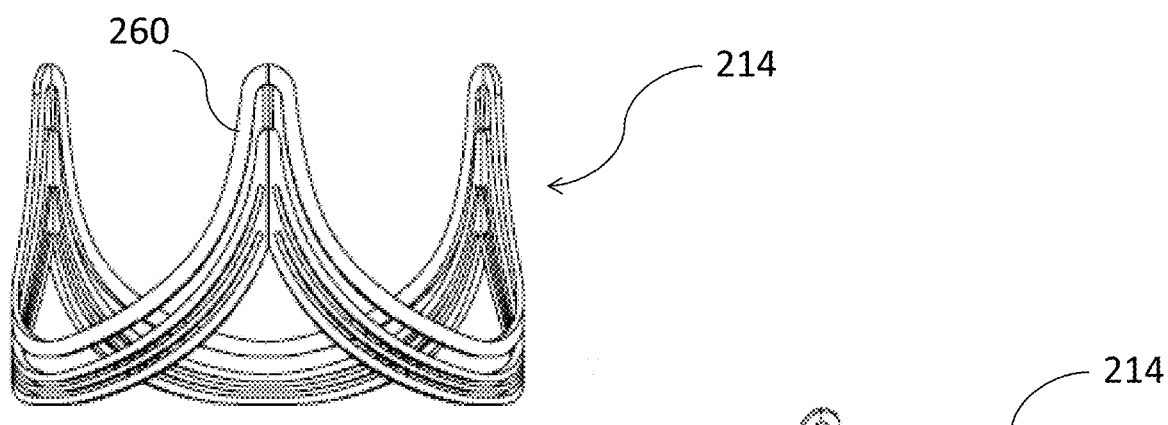
FIG. 23 is a front view of an alternative embodiment of a stent frame.
Figure 24:
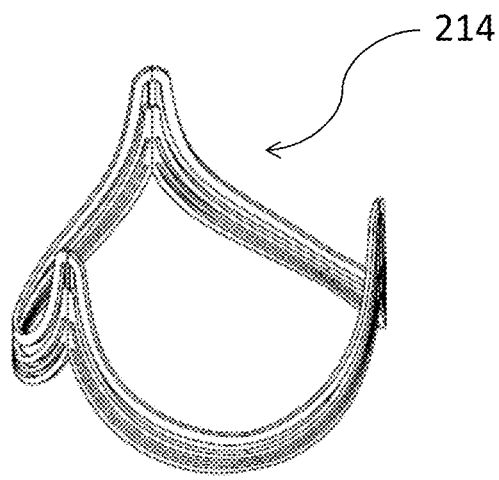
FIG. 24 is a perspective view of the stent frame of FIG. 23.

As shown in FIGS. 18-20, the stent frame 114 may include multiple upper frame portions (as discussed in FIG. 13). For example, as shown in FIG. 18, the stent frame 114 may include a first, second, and third upper frame portions 160, 168, and 170. Using the weaving technique described above, a single or multiple pieces of leaflet material may be applied to the stent frame 114. For example, in one embodiment, three separate pieces of leaflet material may be applied to the stent frame 114 by including leaflet extensions that extend from the leaflet material body and may be woven through the various upper frame portions 160, 168, and 170, in order to secure the leaflet material to the frame 114. This technique may reduce the number of sutures needed to secure the material to the frame.

As shown in FIGS. 21-26, in yet other embodiments, a stent frame 214 may be made so that a minimal amount of stent material is needed. In this embodiment, the leaflet material may be woven through the stent frame 214 and an upper frame portion 260, as described above, however when multiple pieces of leaflet material are employed, the leaflet extensions may be disposed though slots 272 formed through the stent frame 214.

Figure 25:
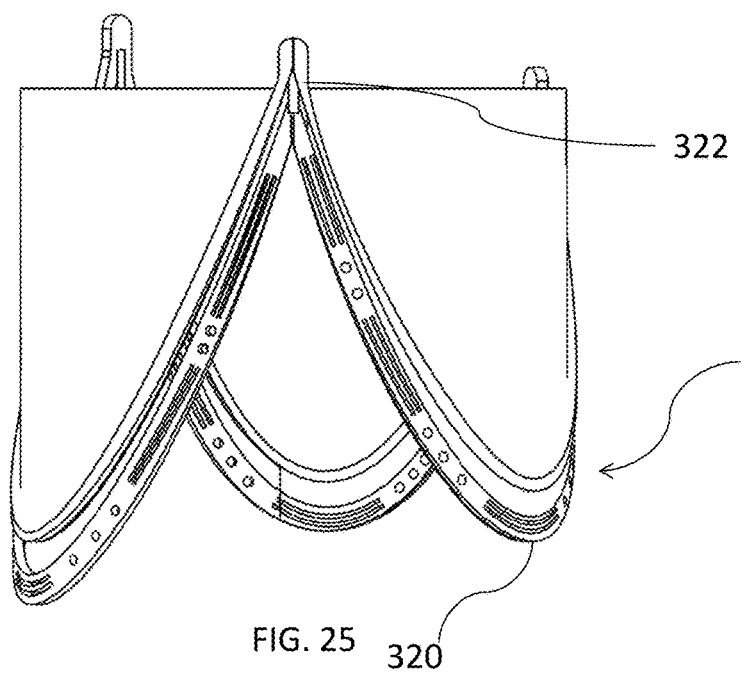
FIG. 25 is a front view of an alternative embodiment of a stent frame.
Figure 26:
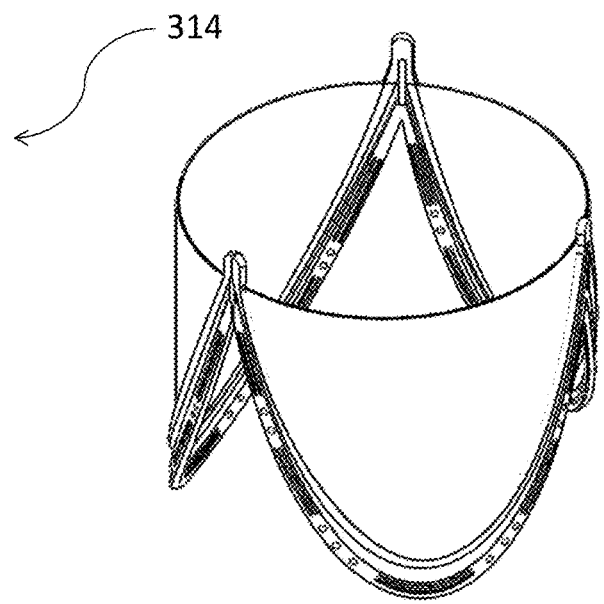
FIG. 26 is a perspective view of the stent frame of FIG. 25.

Referring now to FIGS. 25 and 26, like the stent frame 214 described above, a stent frame 314 is made of a minimal amount of material. In this embodiment, however, the stent frame 314 may be customized to fit individual patients by varying the height of stent posts 322 and the depth of a stent base 320.

The PHV may be implanted into a patient using known surgical techniques. However, it should be appreciated that modifications may be made to the PHV to enable implantation using known trans-catheter methods.

Examples

Figures 27, 28:
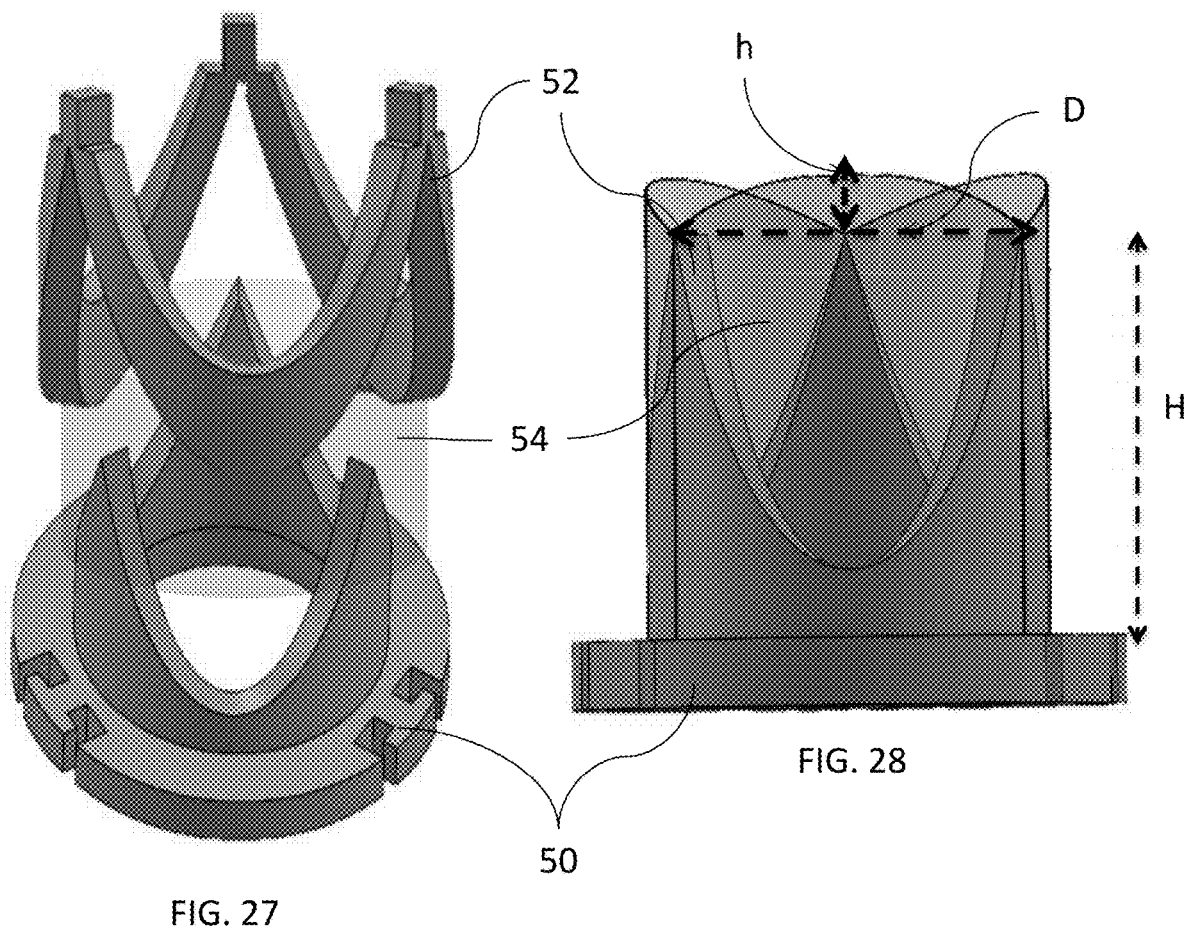
FIG. 27 is an exploded perspective view of an embodiment of a 3D printed model of a prosthetic heart valve.
FIG. 28 is a plan view of an embodiment of a 3D printed model of a prosthetic heart valve.

In order to assess the commissure coaptation and fluid dynamics of the PHV in the ascending aorta, six 3D printed models of the stent and corresponding leaflets were produced to mimic the performance of the PHV. As shown in FIGS. 27 and 28, the models included a stent base 50, a stent clip portion 52, and a sheet of LLDPE leaflet material 54 wrapped around the stent base 50 and disposed between the base 50 and the stent clip portion 52. As shown in FIG. 28, the aspect ratio between stent height and diameter (H/D) was varied for three different PHVs with ratios listed in Table 1, below:

TABLE 1

| Height (H) to Diameter (D) Aspect Ratio | | | |
|---|---|---|---|
| | Low profile (LP) | Medium profile (MP) | High profile (HP) |
| H/D | 0.6 | 0.7 | 0.88 |

Also, the arch height to diameter aspect ratio, herby referred to as h/D, was varied as shown in Table 2, below:

TABLE 2

| Parameters used to design leaflets | | | |
|---|---|---|---|
| | No arch (NA) | Short arch (SA) | Long arch (LA) |
| h/D | 0 | 0.081 | 0.116 |

Those examples having configurations providing full commissure coaptation were studied further, including models with a low profile/no arch (LPNA), low profile/short arch (LPSA), low profile/long arch (LPLA), medium profile/no arch (MPNA), medium profile/short arch (MPSA), and high profile/no arch (HPNA).

Examples 1-6 had a diameter of about 21.5 mm. The stent base 50 had a cylindrical end, which serves to keep the leaflets in place and three stent posts to form the three cusps of the valve. The rectangular piece of LLDPE 54 was cut and wrapped around the stent base 50, creating a cylinder. The LLDPE 54 was fixed to the three stent posts to ensure a symmetric geometry in closed position of the leaflets. Fixing was performed by connecting the stent base 50 to an air vacuum and fixing the LLDPE 54 by matching the three cusps.

In order to mimic the PHV 10, the stent clip portion 52 was placed on top of the LLDPE 54 in a way that created three cusps resembling the tri-leaflet PHV in the normally closed position. The stent base 50 and the stent clip portion 52 were secured together using three orthodontic rubber bands. FIG. 26 shows the assembling process for each of the Examples 1-6.

Flow Loop Setup

Each example valve was inserted into a transparent acrylic aortic chamber machined to mimic the outer walls of an aorta. The chamber was then placed in the aortic position of a left heart simulator that was controlled by an in-house LabVIEW program. The parameters of the left heart simulator were adjusted to simulate the physiological flow and pressure conditions of the aortic valve in the in vitro setup, which were measured using ultrasonic flow probes (Transonic Inc., Ithaca, NY), and the pressure upstream and downstream of the valve was measured with Validyne pressure transducers (Validyne Engineering Corp., Northridge, CA).

An ensemble average of flow curves was obtained over 20 cycles at an average resting condition (Heart Rate (HR)=60 bpm, Mean Aortic Pressure (MAP)=100 mmHg, Cardiac Output (CO)=5 L/min) using the aforementioned LabVIEW program. The working fluid for the flow loop was a mixture of water/glycerin with 38% glycerin concentration to produce a Newtonian blood analog of similar kinematic viscosity and density (v=3.5 cSt, $\rho$=1080 kg/m$^3$).

High Speed Imaging

The example valves' dynamic models were evaluated using high speed imaging and particle image velocimetry (PIV). Both of these were done using the same aortic chamber, obtaining data from front viewing window and lateral side. High speed videos were captured to analyze the overall performance of the designed PHVs and to evaluate leaflet closure. To do this, an acrylic dog-leg chamber was added to the downstream of aortic chamber and a high-speed CMOS camera (FASTCAM SA3, 60 kfps, 1024×1024 px, Photron, Tokyo, Japan) was positioned in front of the dog-leg window. Images were acquired at 1000 fps.

Particle Image Velocimetry

To visualize particle movement during the PIV process, the flow was seeded with PMMA-Rhodamine B seeding particles (microParticles GmbH, Berlin, Germany) with particle sizes ranging from 1 to 20 μm. A laser sheet cut through the center plane of one leaflet and illuminated the particles. The laser sheet was created using a Nd:YLF single-cavity diode-pumped solid-state, high-repetition-rate laser (Photonic Industries, Bohemia, NY) coupled with external spherical and cylindrical lenses and an orange filter. The high-speed camera was placed on the side of aortic chamber to view the laser sheet. Measurements were phase-locked with acquisition of 250 double-frame images at each time point. Commercial PIV software, DaVis (LaVision, Germany), was used for data acquisition and processing.

Velocity vectors were calculated using an advanced PIV cross-correlation method with a 50% overlap multi-pass approach with an initial interrogation window of 64×64 pixels which progressively reduced to 8×8 pixels interrogation window passes. No pre-processing was done, but post-processing was performed using a median filter that rejected vectors outside 2 standard deviations of the neighbor vector. The effective spatial resolution was 27 μm/(pixel) and the temporal resolution was 1000 Hz. Particle seeding density was approximately 0.02 particles per pixel and the particle displacement was around 0-10 pixels per frame (average 5 pixels). The number of particles per interrogation window averaged 20.5 which are acceptable for high-quality PIV. Velocity vectors and vorticity contours were ensemble averaged across 5 trials.

Definition of the Calculated Parameters

The following parameters are used to characterize fluid dynamics in the valve and the flow chamber used as model of the ascending aorta:

Regurgitation fraction: In order to make a comparison between regurgitant fractions that occur in each example valve, flow diagrams obtained from LabVIEW program assigned to the flow loop were analyzed. The regurgitation fraction is the ratio between reverse flow during the time the valve is closed to the total flow in the loop. Leakage percentage is defined as the ratio between the sum of the reverse flows that occur both during valve closure (closing fraction) and the duration of the time the valve is closed to the total flow in the loop (regurgitation fraction).

Effective Orifice Area (EOA): The effective orifice area (EOA) is another parameter to evaluate valve's hemodynamic performance. EOA was calculated using Gorlin equation, in which it is a function of both flow rate and transvalvular pressure gradient.

$$EOA = Q_{rms}/(51.6\sqrt{(\Delta P_{mean})}) \quad (1)$$

Calculations were acquired over 10 cardiac cycles and then averaged to provide the representative values in Table 3.

TABLE 3

Calculated values for the Effective Orifice Area and normalized RSS of each valve model.

| | LPNA | LPSA | LPLA | MPNA | MPSA | HPNA |
|---|---|---|---|---|---|---|
| EOA | 2.57 ± 0.087 | 1.99 ± 0.007 | 2.01 ± 0.415 | 2.74 ± 0.02 | 1.72 ± 0.031 | 1.89 ± 0.013 |
| Normalized RSS | 0.14 ± .008 | 0.023 ± 0.0029 | 0.016 ± 0.0014 | 0.040 ± 0.005 | 0.017 ± 0.0001 | 0.029 ± 0.002 |

The coordinate system used to calculate different parameters are defined so that X direction is along the center plane of the heart valve and Z-direction is perpendicular to our interrogation window. U and V are velocity components respectively along X and Y directions with u' and v' as the velocity fluctuations in each direction.

Vorticity ($\omega_z$): Regions of high vorticity indicate high tendency of fluid elements swirling and rotating along one axis. Even though flow field in aorta is three-dimensional, the vorticity along z-direction is dominant. 2D PIV results along X-Y plane provide vorticity field along Z axis which is defined as follows:

$$\omega_z = (\partial V/\partial x) - (\partial U/\partial y) \qquad (2)$$

Principal Reynolds Shear Stress (RSS): It is known that high shear stress results in destruction of red blood cells (hemolysis). One method to evaluate the performance of designed PHVs is to calculate RSS to obtain the optimal design for minimal blood damage. RSS is a component of total shear stress calculated from Reynolds decomposition of Navier-Stokes equation. RSS is defined as:

$$RSS = \rho \sqrt{(((\overline{u'u'}) - (\overline{v'v'}))/2)^2 + (\overline{u'v'})^2} \qquad (3)$$

Turbulent Kinetic Energy (TKE): This parameter represents the kinetic energy per unit mass for eddies in a turbulent flow. The physiological effect of high TKE is extended exposure of cells to high shear stress and will result in cell membrane rapture, platelet activation and thrombosis. For a 2D PIV, TKE is expressed as:

$$TKE = \frac{1}{2}(\overline{u'^2} + \overline{v'^2}) \qquad (4)$$

Results

Hemodynamics Results

Figure 29:
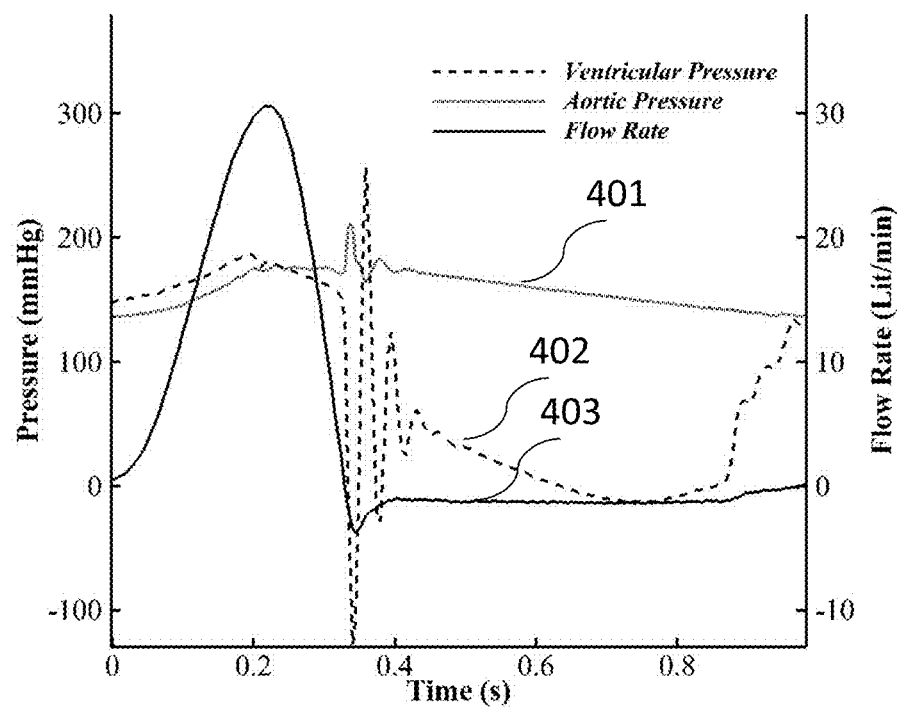
FIG. 29 is a graphical representation of a pressure and flow rates over time for prosthetic heart valve Example 5 with a medium profile and a short arch.

Pressure and flow data were acquired for all six examples from LabVIEW. As shown in FIG. 29, the pressure and flow curve for the MPSA PHV was plotted (series 401 corresponds an aortic pressure cure, series 402 corresponds to a ventricular pressure curve, and series 403 corresponds to a flow rate curve). The flow loop was adjusted to match physiological conditions and the pressure curves for the four valves, except the LPNA, were found to have the same general shape.

Figure 30:
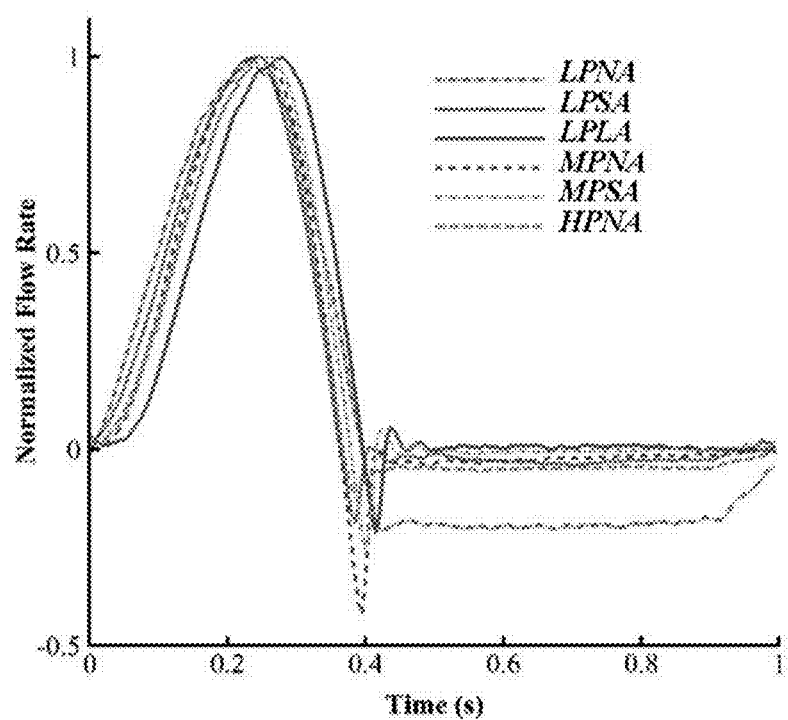
FIG. 30 is a graphical representation of the normalized flow rate over time for prosthetic heart valve Examples 1-6.
Figure 31:
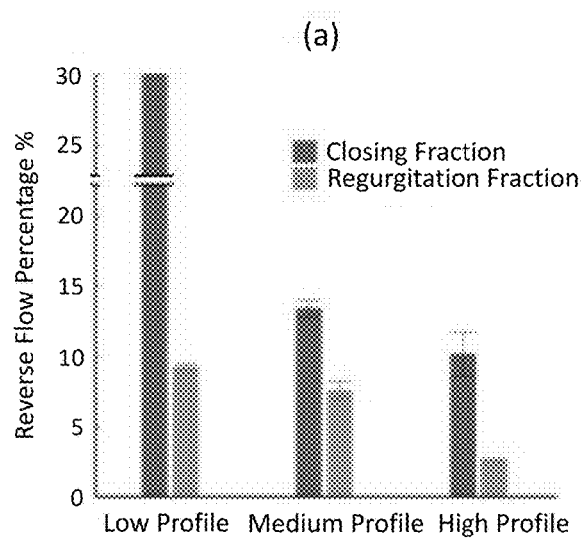
FIGS. 31 and 32 are graphical representations of the reverse flow percentages for the closing and regurgitation fractions of Examples 1-6.
Figure 32:
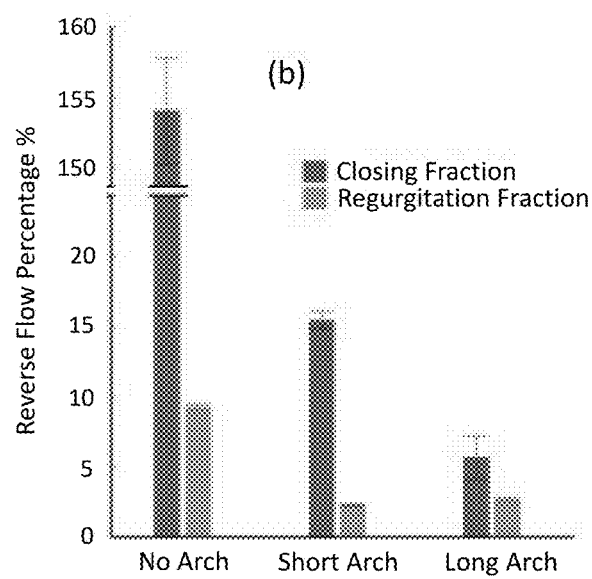

However, the LPNA valve failed to maintain the desired 120/80 mm Hg pressures. Flow was normalized by the maximum flow rate for each valve model and the normalized flow curves for all six valves are presented in FIG. 30. The comparison between flow curves obtained for each valve indicates an improvement in commissure coaptation based on the reduction in back flow as profile length increased or when leaflet arches were added. The regurgitation fraction is further quantified for both H/D and h/D aspect ratios. FIGS. 31 and 32 show a decrease in regurgitation fraction with the increment in H/D and h/D respectively. The error bars in FIGS. 31 and 32 represent the calculated standard deviation for each value.

Leaflet Kinematics

Figure 33:
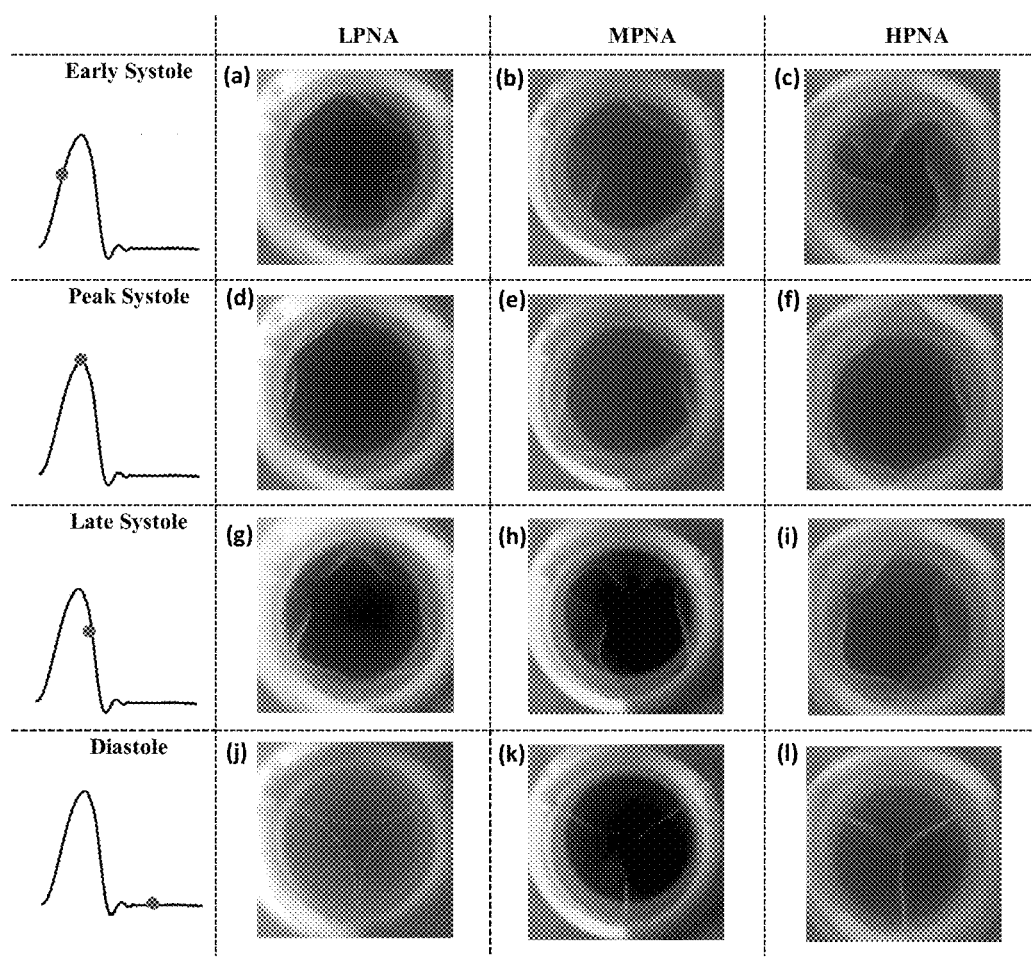
FIGS. 33 and 34 are high speed camera images of Examples 1-6 taken at four time point throughout a typical cardiac cycle.
Figure 34:
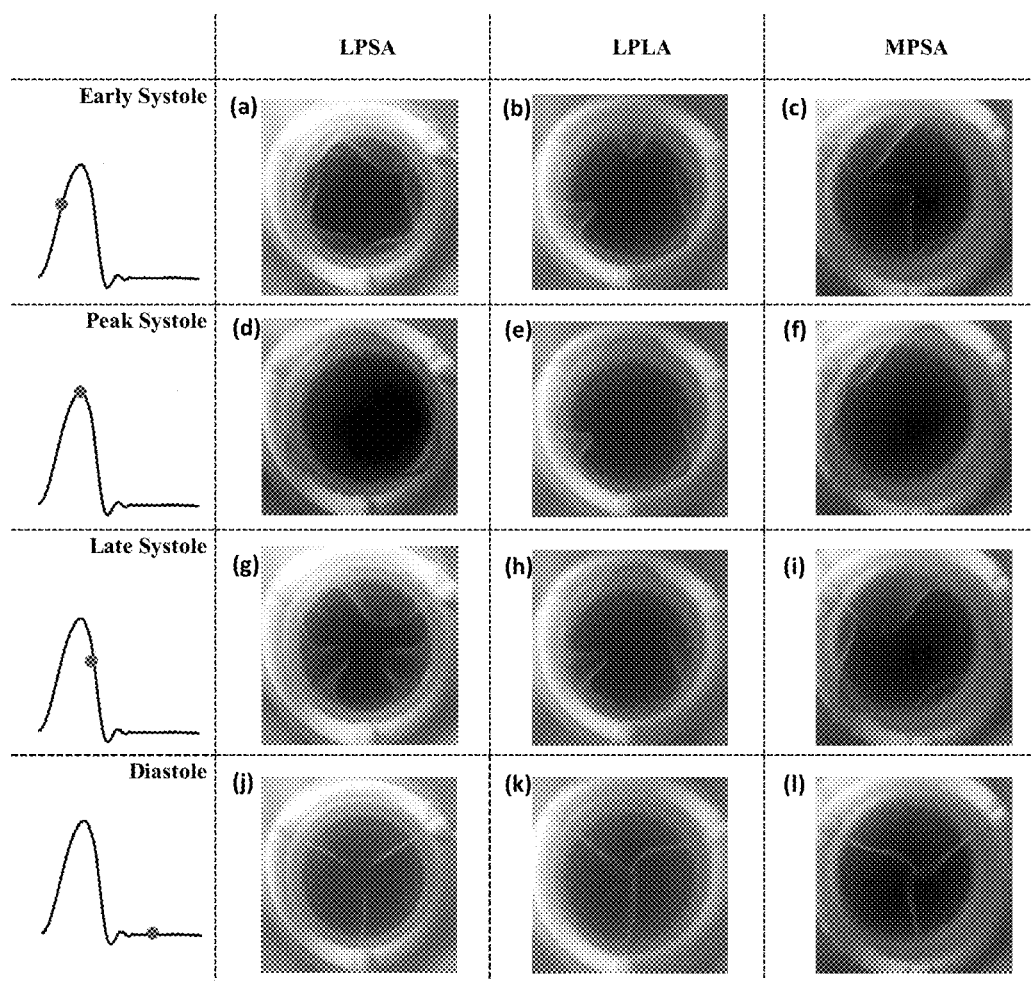

Coaptation kinematics were further studied using high-speed camera images of each valve in the flow loop. Images were acquired during four time points throughout the cardiac cycle: Early Systole (ES), Peak Systole (PS), Late Systole (LS) and Diastole. The first set of experiments were carried out using the three valve model examples without arches to evaluate the effect of H/D (FIG. 33). The second set were for the medium and short profile valves with short and long arch added to their leaflets to study the effect of h/D (FIG. 34). As observed in FIGS. 33 and 34, the large gap at the center of commissures in the LPNA valve is diminished as either the stent profile or the arch length increase. This observation indicates the increment in commissural contact as the aspect ratio and arch height increase.

The LPLA valve in FIG. 34 shows warping of commissures at diastole and small amount of asymmetry at PS. FIG. 33 also indicates that obtaining a symmetrical leaflet opening is easier when the leaflets have no arch added. MPSA had an asymmetric leaflet opening with a lag time for one leaflet to open all the way which can result in undesired fluid motion during early systolic phase.

Quantitative Flow Results

High resolution PIV was used to capture turbulent characteristics through the aortic valve and ascending aorta. Ensemble averaged velocity vectors superimposed by vorticity contours are shown at two time points (ES and PS) throughout the cardiac cycle for each PHV in the left panels of FIG. 35 and FIG. 36 to show the effect of stent height and leaflet arch respectively. As illustrated, the averaged velocity vectors for the six example PHVs are plotted based on the scale bar representing vorticity in a unit of inverse seconds ($s^{-1}$). At early systole (ES) the examples with an arch result in an asymmetric velocity profile skewed toward the top along the centerline of the chamber. No significant difference was observed in the values for velocity for each example. The maximum velocity during ES was ranged from 1.3 m/s for MPNA to 1.8 m/s for LPLA. The flow streamlines for LPLA and MPSA were curved, showing a downward motion towards lower part of the flow chamber and then upward motion to obtain a straight streamline through the rest of the measurement plane.

The central orifice jet in short profile valves initiated perfectly symmetric during ES, however during PS the central jet for LPNA showed an upward motion at the trailing edge of the leaflet and resulted in larger separation region in the lower portion of the chamber. Except for LPSA, the other PHVs produced separation zone only on the lower part of the flow chamber, corresponding to the side of the valve with the stent post, as opposed to a free leaflet edge. No reattachment point was observed for the HPNA PHV in the measurement plane; while the rest of the PHVs showed reattachment points in 1-2 diameters downstream of the annulus (e.g., the distance from the annulus to the reattachment point is between 1 to 2 times the diameter of the respective valve size), as observed in FIGS. 37 and 38. Maximum velocity during PS is assigned to LPNA and was measured 3.1 m/s.

Maximum peak velocity for the other PHVs ranged between 1.8 m/s to 2.2 m/s. The velocities downstream of the trailing edge of the leaflet during diastole were typically less than 0.1 m/s for all the examples except for LPNA and MPNA which were measured 0.35 m/s and 0.17 respectively. The reason for higher diastolic velocity in these two PHVs was the presence of a leakage jet at the center of the commissural region. The velocity for this leakage jet was 0.7 m/s and 0.2 m/s for LPNA and MPNA models respectively.

RSS and TKE Distribution

Figure 35:
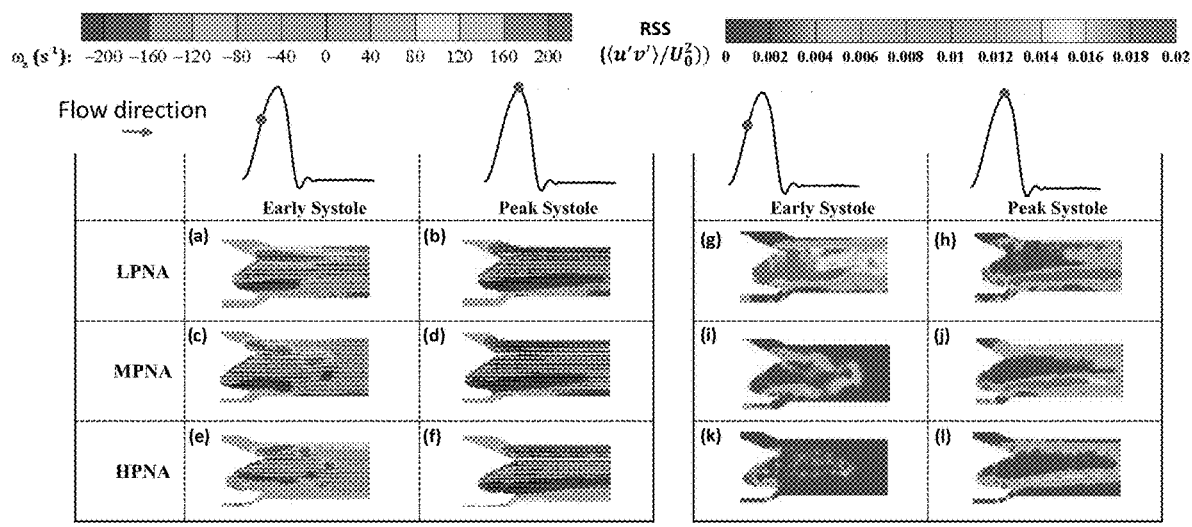
FIGS. 35 and 36 are graphical representations of averages velocity vectors superimposed by vorticity contours and contours of normalized Reynolds shear stress at two time points throughout the cardiac cycles for Examples 1-6.
Figure 36:
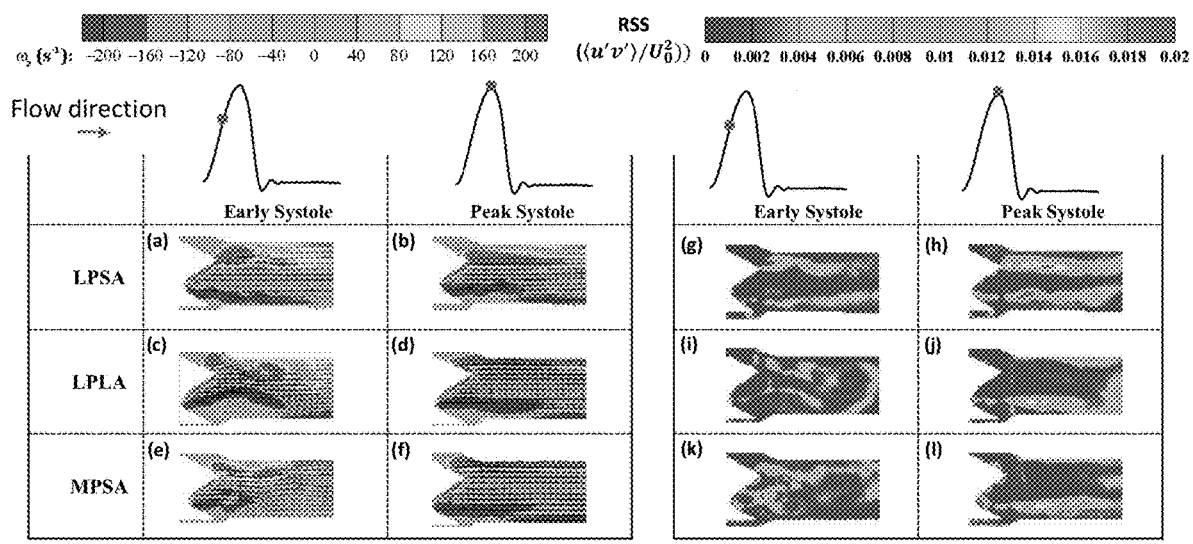

Reynolds shear stress (RSS) is a critical parameter in predicting blood damage and calcification in heart valves. Contours of normalized RSS near PHV leaflets and inside the ascending aorta are provided in the right panels in FIGS. 35 and 36, for varying stent profile and arch length to study the propensity of blood cell damage in each of the six examples. Normalized values were calculated to take the difference in peak velocity for each example into account. As illustrated, the normalized RSS for the six PHVs are plotted based on the scale bar representing RSS (e.g., a unitless number). The highest value for RSS is observed in the LPNA during PS, which is 1940 dyne/cm2 with normalized RSS value of 0.14±0.008. Adding leaflet arches as well as increasing aspect ratio decreased RSS one order of magnitude. However, MPNA showed higher normalized RSS values in comparison to the other four valve, and was measured to be 0.04±0.004. The LPLA valve configuration resulted in the smallest value of normalized RSS, which was 0.016±0.0014. The measured valued for normalized RSS is presented in Table 3, above. Generally high regions of RSS were observed in the shear layer region between the central orifice jet and at the trailing edge of the leaflets. As shown in FIGS. 35 and 36, regions of high RSS values were diminished when arches were added to the leaflets.

Contours of TKE bear a resemblance to RSS plots shown in FIGS. 35 and 36. LPNA had highest magnitudes of TKE, corresponding to higher levels of kinetic energy for turbulent eddies. Similar to RSS, TKE was also decreased with the addition of leaflet arches and increment in aspect ratio.

Discussion

Effect of Heart Valve Profile

Hemodynamics and Kinematics of Leaflets

One major parameter that needs to be taken into account for the AV hemodynamics is to ensure a negligible regurgitation fraction during diastole to minimize the work of the heart and avoid a high shear stress jet that can induce platelet activation and hemolysis. Appropriate sealing of the leaflets is obtained through a proper aspect ratio or a modified leaflet design. Generally, short profile heart valves are more desirable due to the reduced dead space by diminishing the blockage of coronary ostium and aortic sinuses. The dead space created in higher profile PHVs supports coagulation and will increase the risk for thromboembolic complications.

The high-speed camera snapshots shown in FIG. 33 indicate that the aspect ratio of LPNA and MPNA models was not large enough to cover the central gap, which leads to flow regurgitation throughout diastole. The regurgitant flow in these two valve models can be detected in the diastolic phase of the cardiac cycle.

All designed models were able to withstand the physiological flow and pressure condition except for the LPNA model which showed higher pressure drops across the PHV during systolic phase. This is due to the increment in the peak flow rate to maintain an average flow rate compensating for regurgitation.

Based on the EOA values provided in Table 3, the highest value for EOA was achieved in the MPNA valve. A decrement in EOA was observed in the HPNA valve, which is likely due to the fact that the larger leaflets take more time to fully open. The EOA for LPNA valve is shown to be relatively high, and this is likely due to the fact that LPNA valve configuration was not able to withstand normal pressure gradient of 80-120 mmHg.

Velocity and Vorticity Results

Figure 37:
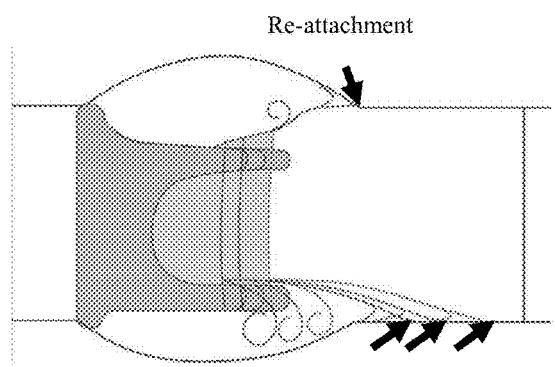
FIGS. 37 and 38 are graphical depictions of hemodynamics for prosthetic heart valves having a no arch and varying profiles and varying arch heights, respectively.

The Velocity and vorticity pattern observed in the center orifice jet shows a great dependence to the PHV geometry. LPNA and MPNA models created jets with higher systolic peak velocity throughout the ascending aorta. The higher downstream velocity present in these models is to compensate for the regurgitating flow during diastole and keep the average flow rate at the desired value of 5 L/s. No reattachment points were observed for the lower part of the HPNA model in our view plane. The reason for delayed reattachment appears to be the presence of longer stent posts act as a barrier and create a larger turbulent shear zone which delays reattachment (FIG. 37). This implies leaflet coaptation does not necessarily correlate to an optimum PHV geometry.

Comparing all three examples together shows that the central orifice jet for the MPNA valve models achieved unidirectional flow sooner than the other two models by creating reattachment points in the 1D downstream of the trailing edge of the leaflets.

Effect of RSS and TKE

High values of RSS are strongly correlated to hemolysis and blood damage. The RSS values reduced dramatically as a result of an enhanced leaflet coaptation. The high values of RSS and TKE were more dominantly observed in the LPNA and MPNA valve models, which shows the contribution of the leakage jet in increasing the risk of blood damage. The HPNA model also resulted in larger values of RSS and TKE throughout the ascending aorta. The values measured for RSS in these examples is well below the results found previously, however they still are above the reported values for RSS threshold (~400 dyne/$cm^2$) suggested by previous studies which can cause hemolysis and platelet activation.

Effect of Leaflet Arch

Leaflet Kinematics

The results indicate that leaflet arch dramatically improves commissure coaptation. The leakage flow percentage reduced from 150% in the LPNA model to 5.6% in the LPLA configuration. As a result the maximum PS downstream velocity reduced to 58% of its value in LPNA to 1.8 m/s in LPSA valve model. Additionally, maximum RSS value reduced 40% from the LPNA to LPLA model. Increments in leaflet arch length resulted in warping in the leaflet tips during diastole, which can increase the chance of fatigue. Warping was observed in the LPLA and became more noticeable for the MPSA, which also resulted in reduced EOA. An asymmetric leaflet opening and closing seen for MPSA example (FIG. 34) is associated with the warping of the leaflets in their closed position. Long leaflet arches resulted in one leaflet being pushed underneath the other two which is another reason of the asymmetric opening and closing of the MPSA example.

Additionally, the EOA value for the MPSA is lower than LPSA and LPLA and this can be due to the larger size of leaflets and the lag in the opening time compared to the other two.

Velocity and Vorticity Results

Figure 38:
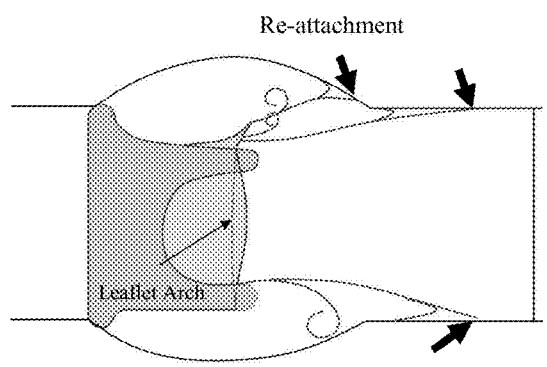

FIG. 37 shows jets of fluid through PHVs with different stent profiles (e.g., low profile, medium profile, high profile) and FIG. 38 shows jets of fluid through PHVs with different leaflet arch (e.g., no arch, arch). In FIG. 37, the blue, red, and green profiles correspond to jets of fluid for the LPNA, MPNA, and HPNA models, respectively. In FIG. 38, the blue and red profiles correspond to jets of fluid for the LPNA and LPSA models, respectively. In both figures the black arrows indicate where reattachment points to the aortic wall occur for the respective valve design. Earlier reattachment points were observed in both top and bottom sections of the ascending aorta for LPLA and MPNA models. The flexible arches may create a wider opening for the jet of fluid exiting through the PHV. As shown in the schematic drawing in FIG. 37, due to Coanda effect the fluid jet stays attached to the arch surface and this attachment deviates flow from the straight path guiding the flow to a higher point in the sinus area. Moreover, increasing the exit diameter as the starting flow develops results in higher-energy vortex ring structures with peak vorticity located further from the axis of symmetry relative to a static nozzle case. The flexible arches facilitate transfer of impulse to a greater volume of fluid and result in an enhanced turbulent mixing as well as helping the flow to slow down. This reveals the critical role that leaflet arches play in damping velocity fluctuations and initiates sooner reattachment. Hence, reduces the residence time in recirculation zones and decreases the chance of platelet activation and blood damage.

Even though arches provided earlier reattachment to the ascending aorta, the added arch increases leaflet area, requiring more pressure to open the leaflet all the way. The delayed opening of flaps during early systolic pushes the fluid towards the center of the chamber, resulting in vortex rings in the trailing edge of the leaflets (FIG. 36). Viscous Shear Stress (VSS) data presents much lower values for all six valve models in comparison to mechanical heart valves, indicating a much lower blood damage potential.

Effect of RSS and TKE

The RSS values reduced dramatically, since the reduced leakage associated with coaptation resulted in reduced peak flow to maintain an average cardiac output. Additionally, the presence of arches at leaflet tips could act as damping mechanism by providing a variable exit diameter for the orifice jet and reduce RSS and TKE values.

Combined Effects and Interactions

Comparison of coaptation in MPNA and LPSA indicates commissural contact is more easily accomplished by the addition of leaflet arches. The combination of leaflet arch and increased profile height observed in MPSA design led to better overall hemodynamic performance. This is due to the fact that longer arches increase asymmetric leaflet opening due to warping; therefor, making short arches preferable.

Generally, it was demonstrated that leaflet arches and higher heart valve profile provide several advantages such as: 1) resulting in a dramatic decrease in the RSS, 2) yielding to better leaflet coaptation, and 3) minimizing regurgitation percentage. However, high stent profile may delay reattachment of flow in the aorta and slightly increases RSS. This increment can potentially escalate hemolysis and blood damage. Leaflet arches result in great enhancement of leaflet kinematics and PHV hemodynamics by optimizing the low profile design of the heart valve.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "substantially" is used in the specification or the claims, it is intended to take into consideration the degree of precision available or prudent in manufacturing. To the extent that the term "operably connected" is used in the specification or the claims, it is intended to mean that the identified components are connected in a way to perform a designated function. As used in the specification and the claims, the singular forms "a," "an," and "the" include the plural. Finally, where the term "about" is used in conjunction with a number, it is intended to include ±10% of the number. In other words, "about 10" may mean from 9 to 11.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

The invention claimed is:

1. A prosthetic heart valve comprising:
a stent frame comprising a base comprising at least two stent posts extending upwardly, a first upper frame portion, a second upper frame portion, and a third upper frame portion connected on top of the at least two stent posts via stent frame extensions,
   wherein the first upper frame portion has a shape mimicking that of an upper edge of and between the at least two stent posts of the base, a lower edge of the second upper frame portion has a shape that is similar to an upper edge of the first upper frame portion, and a lower edge of the third upper frame portion has a shape that is similar to an upper edge of the second upper frame portion, and
   wherein the first upper frame portion connects to the at least two stent posts only at each of top points of the at least two stent posts by the stent frame extensions, the second upper frame portion connects to the first upper frame portion only at each of top points of the first upper frame portion by the stent frame extensions, and the third upper frame portion connects to the second upper frame portion only at each of top points of the second upper frame portion by the stent frame extensions; and
a leaflet material having an upper portion with at least two arches extending upwardly therefrom and
the leaflet material is secured to the stent frame by having the leaflet material weaving through the stent frame between the upper edge of the at least two stent posts of the base and the first upper frame portion, between the first and the second upper frame portions, and between the second and the third upper frame portions.

2. The prosthetic heart valve of claim 1, wherein the leaflet material is disposed on an outer surface of the stent frame at the base.

3. The prosthetic heart valve of claim 2, wherein the leaflet material weaves through the stent frame from the outer surface to an inner surface between the first upper frame portion and the at least two stent posts of the base.

4. The prosthetic heart valve of claim 1, wherein the leaflet material is disposed on an inner surface of the stent frame at the base.

5. The prosthetic heart valve of claim 1, wherein the base has a lower edge having a shape that is similar to a lower edge of the first upper frame portion.

6. The prosthetic heart valve of claim 1, wherein the at least two stent posts have heights that are different from one another.

7. The prosthetic heart valve of claim 1, wherein the leaflet material comprises multiple pieces.

8. The prosthetic heart valve of claim 1, wherein the leaflet material comprises linear low density polyethylene, polytetrafluoroethylene, low-density polyethylene, polyethylene terephthalate, polypropylene, polyurethane, polycaprolactone, polydimethylsiloxane, polymethylmethacrylate, polyoxymethylene, thermoplastic polyurethane, or combinations thereof.

9. The prosthetic heart valve of claim 1, wherein the leaflet material is made of linear low density polyethylene.

10. The prosthetic heart valve of claim 1, wherein the leaflet material further comprises hyaluronic acid.

11. The prosthetic heart valve of claim 1, wherein the stent frame has a height and an inner diameter, and wherein a ratio of the height to the inner diameter is from about 0.5 to about 0.9.

12. The prosthetic heart valve of claim 1, wherein the at least two arches have a height, and wherein a ratio of the height of the at least two arches to an inner diameter of the stent frame is from about 0.05 to about 0.12.

13. The prosthetic heart valve of claim 1, wherein the leaflet material comprises a bioprosthetic material.

14. The prosthetic heart valve of claim 1, wherein the leaflet material is a continuous sheet of leaflet material with notches in the upper portion, and each of the notches is located between two of the at least two arches.

15. The prosthetic heart valve of claim 14, wherein the leaflet material has a three dimensional curvature.

16. The prosthetic heart valve of claim 1, wherein the first upper frame portion gathers the leaflet material and enables the leaflet material to mimic function of a native aortic heart valve cusp, opening and closing with a flow of blood through the prosthetic heart valve.

\* \* \* \* \*